United States Patent [19]
Fuhrman

[11] Patent Number: 5,437,272
[45] Date of Patent: Aug. 1, 1995

[54] PERFLUOROCARBON ASSOCIATED GAS EXCHANGE

[75] Inventor: Bradley P. Fuhrman, Pittsburgh, Pa.

[73] Assignee: Alliance Pharmaceutical Corp., San Diego, Calif.

[21] Appl. No.: 694,290

[22] Filed: May 1, 1991

[51] Int. Cl.$^6$ ............................................. A61M 15/00
[52] U.S. Cl. ........................ 128/203.12; 128/204.18; 128/913
[58] Field of Search ............... 128/204.18, 913, 203.12

[56] References Cited

U.S. PATENT DOCUMENTS

| | | | |
|---|---|---|---|
| 3,975,512 | 6/1991 | Long | 424/5 |
| 4,036,210 | 7/1977 | Campbell et al. | |
| 4,825,859 | 5/1989 | Lambert | 128/202.16 |
| 5,024,995 | 6/1991 | Robertson et al. | 514/21 |
| 5,029,580 | 7/1991 | Radford et al. | 128/207.14 |

FOREIGN PATENT DOCUMENTS

| | | |
|---|---|---|
| 858824 | 8/1981 | U.S.S.R. |
| 1143420 | 3/1985 | U.S.S.R. |
| WO91/03267 | 3/1991 | WIPO |

OTHER PUBLICATIONS

Greenspan, et al., "Liquid Ventilation of Preterm Baby", Lancet, Nov. 4, 1989, p. 1095.

Widjaja, et al., "Mechanical Properties of Isolated Fetal Miniature Pig Lungs After Substitution . . . ", Res. Exp. Med., 188:425-432 (1988).

Waldrop, "The (Liquid) Breath of Life", Science, 245:1043-1045 (1989).

Richman, et al., "Lung Lavage with Oxygenated Fluoracarbon Improves Gas Exchange and Lung Compliance in Cats with Acute Lung Injury", 1990 World Conference on Lung Health, Category 26.

Curtis, et al. "Airway and Alveolar Pressures During Perfluorocarbon Breathing in Infant Lambs" J. Appl. Physiol. 68: 2322-2328 (1990).

Curtis, et al. "Cardiac Output During Liquid (Perfluorocarbon) Breathing in Newborn Piglets" Crit. Care Med. 19(2): 225-230 (1991).

Merritt, et al. "Exogenous Surfactant Treatments for Neonatal Respiratory Distress Syndrome and their Potential Role in the Adult Respiratory Distress Syndrome" Drugs 38(4): 591-611 (1989).

Nakayama, et al. "Pulmonary Dysfunction in Surgical Conditions of the Newborn Infant" Crit. Care Med. 19(7): 926-933 (1991).

Ravenscraft, et al. "Components of Excess Ventilation in Patients Initiated on Mechanical Ventilation" Crit. Care Med. 19(7): 916-925 (1991).

Richman, P. "Lung Lavage with Oxygenated Fluorocarbon Improves Gas Exchange and Lung Compliance in Cats with Acute Lung Injury" *1990 World Conference on Lung Health*.

Riess, J. "Reassessment of Criteria for the Selection of Perfluorochemicals for Second-Generation Blood Substitutes: Analysis of Structure/Property Relationships" Aritificial Organs 8(1):44-56 (1984).

Shaffer, et al. "The Effects of Liquid Ventilation on Cardiopulmonary Function in Preterm Lambs" Chest Res. 7:303-306 (1983).

Yokoyama, et al. "A Perfluorochemical Emulsion as an Oxygen Carrier" Artificial Organs 8(1):34-40 (1984).

(List continued on next page.)

Primary Examiner—Edgar S. Burr
Assistant Examiner—Aaron J. Lewis
Attorney, Agent, or Firm—Knobbe, Martens, Olson & Bear

[57] ABSTRACT

Method and means for maintaining respiratory gas exchange, by introducing into the pulmonary air passages of a mammalian host a volume of perfluorocarbon liquid substantially equivalent to the pulmonary functional residual capacity of the host, maintaining respiratory gas exchange in the perfluorocarbon liquid-laden pulmonary air passages by continuous positive pressure breathing with a conventional respirator, for up to an hour or more, and thereafter evaporating the perfluorocarbon liquid from the pulmonary air passages. Useful for treating pulmonary surfactant deficiency or dysfunction.

18 Claims, 7 Drawing Sheets

OTHER PUBLICATIONS

Klystra, J. A., et al., Of mice and fish *Transactions of the American Society for Artificial Internal Organs* 8:378–383, 1962.

Reufer, R., Surfactant and alveolar surface forces after breathing of an inert fluoridated liquid, *Federation Proceedings* 29(5):1813–1815, 1970.

Clark, L. C., and F. Gollan, Survival of mammals breathing organic liquids equilibrated with oxygen at atmospheric pressure, *Science* 152:1755–1756, 1966.

Biro, P. B., and P. Blais, Perfluorocarbon blood substitutes, *CRC Critical Reviews in Oncology/Hematology* 6(4):311–374, 1987.

Modell, J. H., et al., Long-term survival of dogs after breathing oxygenated perfluorocarbon liquid, *Federation Proceedings* 29(5):1731–1739, 1970.

Modell, J. H., et al., Liquid ventilation of primates, *Chest* 69:79–81, 1976.

Calderwood, H. W., et al., Residual levels and biochemcial changes after ventilation with perfluorinated liquid, *Journal of Applied Physiology* 139:603–607, 1975.

Forman, D., et al., A fine structure study of the liquid-ventilated new rabbit, *Federation Proceedings* 43:647, 1984.

Rufer, R., and L. Sbitzer, Liquid ventilation in the respiratory distress syndrome, *Chest* 66(Suppl):29–30, 1974.

Puchetti, B., et al., Liquid ventilation in man: first clinical experiences on pulmonary unilateral washing fluorocarbon liquid, Fourth World Congress for Bronchology (Abstracts), p. 115, 1984.

Shaffer, T. H., A brief review: liquid ventilation, *Undersea Biomedical Research* 14(2):169–179, 1987.

Shaffer, T. H., et al., The effects of liquid ventilation on cardiopulmonary function in preterm lambs, *Pediatric Research* 17:303–306, 1983.

Shaffer, T. H., et al., Physiological effects of ventilation with liquid fluorocarbon at controlled temperatures, *Undersea Biomedical Research* 11(3):287–298, 1984.

Lowe, C. A., and T. H. Shaffer, Increased pulmonary vascular resistance during liquid ventilation, *Undersea Biomedical Research* 8(4):229–238, 1981.

Gollan, F., and L. C. Clark, Prevention of bends by breathing an organic liquid, *Transactions of the Association American Physicians* 29:102–109, 1967.

Sass, D. J., et al., Liquid breathing: prevention of pulmonary arteriovenus shunting during acceleration, *Journal of Applied Physiology* 32:451–455, 1972.

Avery, M. E., and J. Mead, Surface properties in relation to atelectasis and hyaline membrane disease, *Am J Dis Child* 97:517, 1959.

Pattle, R. E., et al., Inability to form a lung-lining film as a cause of the respiratory-distress syndrome in the newborn, *Lancet ii*:469, 1962.

Holm, B. A., and S. Matalon, Role of pulmonary surfactant in the development and treatment of adult respiratory distress syndrome, *Anesth Analg* 69(6):805, 1989.

Wolfson, M. R., et al., A new experimental approach for the study of cardiopulmonary physiology during early development, *J Appl Physiol* 65(3):1436, 1988.

Greenspan, J. S., et al., Liquid ventilation of human preterm neonates, *J Pediatr* 117(1 Part 1):106, 1990.

Fuhrman, B. P., Perfluorocarbon liquid vetilation: the first human trial, *J Pediatr* 117(1 Part 1):73, 1990.

Shaffer, T. H., et al., Cardiopulmonary function in very preterm lambs during liquid ventilation, *Pediatr Res* 17:680, 1983.

Barrow, R. E., Volume-pressure cycles from air and liquid filled intact rabbit lungs, *Respiration Physiology* 63:19, 1986.

Avery, M. E., et al., The inflationary force produced by pulmonary vascular distension of excised lungs: the possible relation of this force to that needed to inflate the lungs at birth, *J Clin Invest* 38:456, 1959.

Avery, M. E., and B. D. Fletcher, The Lung and Its Disorders in the Newborn Infant, Third Edition, Philadelphia, WB Saunders, p. 216, 1974.

Calderwood, H. W., et al., Pulmonary lavage with liquid fluorocarbon in a model of pulmonary edema, *Anesthesiology* 38(2):141A, 1973.

Shaffer, T. H., et al., Pulmonary lavage in preterm lambs, *Pediatr Res* 12:695, 1978.

Shaffer, T. H., and G. D. Moskowitz, Demand-controlled liquid ventilation of the lungs, *J Appl Physiol* 36:208, 1974.

Gollan, F., et al., Compliance and diffusion during respiration with fluorocarbon fluid, *Federation Proceedings* 29(5):1725, 1970.

Shaffer, T. H., et al., Gaseous exchange and acid-base balance in premature lambs during liquid ventilation since birth, *Pediat Res* 10:227, 1976.

Shaffer, T. H., et al., Liquid ventilation: effects on pulmonary function in distressed meconium-stained lambs, *Pediat Res* 18(1):47, 1984.

Fuhrman, B. P., et al., Perfluorocarbon (PFC) associated gas exchange (PAGE), *Pediat Res* 29(4 Part II):28A, abstract 199, Apr. 1991.

PERFLUOROCARBON ASSOCIATED GAS EXCHANGE

TECHNICAL FIELD

This invention provides respiratory methods and devices, involving means for supplying respiratory gas under positive pressure, to maintain respiratory gas exchange in perfluorocarbon liquid-filled pulmonary air passages.

BACKGROUND OF THE INVENTION

The present invention relates generally to prior mechanical ventilation and liquid ventilation techniques.

Mechanical ventilators are clinical devices that cause airflow into the lungs. For ventilatory support in the setting of intensive care, volume-controlled or pressure-regulated positive pressure ventilators are generally used. Such devices force air into the lungs during inspiration but allow a return to ambient pressure during spontaneous exhalation. In volume-controlled ventilation, a preset tidal volume is delivered to the patient regardless of the pressure required to deliver the inspiratory volume. In pressure-regulated ventilation, peak inspiratory pressure is limited, as determined by the operating console. Controls are typically also provided to select the inspired $O_2$ mixture, inspiration and expiration time, and ventilatory frequency. Such conventional ventilators are available from several manufacturers.

Liquid ventilation is a radically different technique that involves temporarily filling pulmonary air passages with an oxygenated liquid medium. It was first demonstrated that mammals submerged in hyperoxygenated saline could breathe liquid and successfully resume gas breathing in 1962 (1; see appended Citations). However, this approach to liquid ventilation (LV) was eventually abandoned, due to the practical difficulties of dissolving sufficient quantities of $O_2$ in saline (even at hyperbaric pressures), and because saline rinses away much of the surfactant lining the lung alveoli (2). These problems were overcome in 1966 by Dr. Leland Clark, who was the first to use perfluorocarbon liquids (now oxygenated at atmospheric pressure) to support the respiration of mice, cats, and puppies (3).

Perfluorocarbon (PFC) liquids are derived from common organic compounds by the replacement of all carbon-bound hydrogen atoms with fluorine atoms. These liquids are clear, colorless, odorless, nonflammable, and essentially insoluble in water. PFC liquids are denser than water and soft tissue, and have low surface tension and, for the most part, low viscosity. Perfluorocarbon liquids are unique in their high affinity for gases, dissolving more than 20 times as much $O_2$ and over 3 times as much $CO_2$ as water. Like other highly inert carbonfluorine materials, perfluorocarbon liquids are extremely nontoxic and biocompatible. For a review, see (4).

To date it has been clearly established that mammals can breathe (total ventilation support) oxygenated perfluorocarbon liquids for long periods (>3 hours) and return to gas breathing without untoward long-term effects (5,6). Additional studies have shown that no adverse morphological, biochemical, or histological effects are seen after perfluorocarbon ventilation (7,8). Perfluorocarbon liquids have also been investigated for lung lavage (washing) (9), and have been found to be effective in rinsing out congestive materials associated with Respiratory Distress Syndrome (RDS) in adult humans (10). While total respiratory support of both lungs via perfluorocarbon liquids is not without side effects, these effects are minor and transient (mild acidosis, lower blood $pO_2$, increased pulmonary vascular resistance, and decreased lung compliance) (11-14). Other biomedical applications of perfluorocarbon liquid ventilation have received serious research effort (15,16). Lung cancer hyperthermia via ultrasound and/or convection with perfluorocarbon liquids has been reported (17).

In particular, perfluorocarbon liquid ventilation is a promising treatment of respiratory distress syndromes involving surfactant deficiency or dysfunction. Elevated alveolar surface tension plays a central role in the pathophysiology of the Respiratory Distress Syndrome (RDS) of prematurity (18,19) and is thought to contribute to lung dysfunction in the Adult Respiratory Distress Syndrome (20). Perfluorocarbon liquid ventilation is effective in surfactant-deficient premature animals because it eliminates air/fluid interfaces in the lung and thereby greatly reduces pulmonary surface tension (11). Liquid ventilation can be accomplished at acceptable alveolar pressures (21) without impairing cardiac output (22) and provides excellent gas exchange even in very premature animals (23). A successful human trial of perfluorocarbon liquid ventilation in very premature infants with RDS has recently been reported (24). Recall that, in liquid ventilation, perfluorocarbon liquid is extracorporeally oxygenated and purged of carbon dioxide, and tidal breaths of the liquid are mechanically cycled into and out of the lungs using an investigational device. Unfortunately, such extracorporeal liquid ventilators are not commercially available. Moreover, enthusiasm has also been dampened by the apparent lack of a safe fall-back support system to protect the patient should it be necessary to suddenly discontinue the liquid breathing treatment. Furthermore, because the perfluorocarbon is oxygenated and purged of carbon dioxide outside the body, and cyclically delivered to the lungs, a large and expensive priming volume of perfluorocarbon is required to fill the liquid breathing device. Such operational disadvantages and safety concerns have greatly hindered more widespread use of the otherwise promising liquid ventilation techniques.

SUMMARY OF THE INVENTION

The present invention overcomes the above-stated disadvantages by providing a perfluorocarbon associated gas exchange method that differs mechanistically from either continuous positive pressure breathing or liquid ventilation. The subject method involves introducing into the pulmonary air passages of a mammalian host a volume of perfluorocarbon liquid substantially equivalent to the pulmonary functional residual capacity of the host. Respiratory gas exchange is thereafter maintained (e.g., for an hour or more) in the perfluorocarbon liquid-laden pulmonary air passages by continuous positive pressure breathing, using a conventional gas ventilator. Following this treatment, the perfluorocarbon liquid is allowed to evaporate from the pulmonary air passages.

The data presented below indicates that perfluorocarbon associated gas exchange is virtually as efficient a means of ventilation and gas exchange as continuous positive pressure breathing in normal piglets. Furthermore, perfluorocarbon associated gas exchange provided adequate gas exchange at airway pressures comparable to those of volume-regulated continuous positive pressure breathing.

Like liquid ventilation, perfluorocarbon associated gas exchange confers special advantages in the treatment of surfactant deficiency or dysfunction, yet perfluorocarbon associated gas exchange does not require either extracorporeal oxygenation or cyclic delivery of perfluorocarbon "liquid breaths" to the lungs. As a result, further refinement of investigational instrumentation is no longer a prerequisite to the application of perfluorocarbon liquid treatments to surfactant deficiency and other disorders and diseases in the lung. Moreover, because it is predominantly gas, rather than liquid, that moves in tidal fashion with each breath, the airway pressures required to accomplish perfluorocarbon associated gas exchange are far lower than those required to accomplish liquid breathing. Thus, the potential for barotrauma to the pulmonary air passages is alleviated. Another result is that the pulmonary time constant (product of the airways' resistance to fluid flow times compliance) is far lower during perfluorocarbon associated gas exchange than during liquid breathing. This makes it possible to ventilate the patient more rapidly, and to achieve far greater minute ventilation, during perfluorocarbon associated gas exchange than during liquid breathing. Finally, safety concerns associated with potential equipment breakdown are allayed because backup gas ventilators suitable for implementing perfluorocarbon associated for exchange are readily available in general clinical settings.

DETAILED DESCRIPTION OF THE PREFERRED EMBODIMENT

Figure 2:
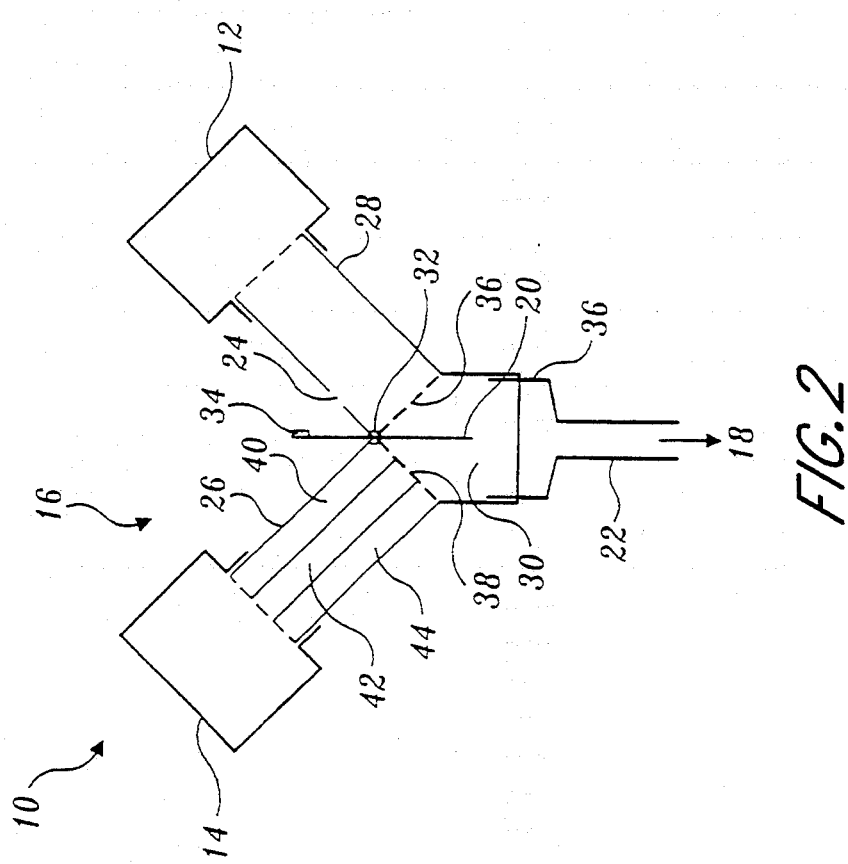
FIG. 2 shows an exemplary PAGE adapter for regulating fluid flow by switching between perfluorocarbon associated gas exchange and continuous positive pressure breathing.

It was, a priori, almost unimaginable that gas can be forced into a liquid-filled lung, and that the gas will then almost completely leave the lung before the liquid is also exhaled. Nevertheless, this disclosure describes such a method of respiratory support, termed Perfluorocarbon Associated Gas Exchange (PAGE), and its successful use in normal piglets. A volume of perfluorocarbon equivalent to the normal pulmonary functional residual capacity was instilled into the trachea and "bubble-oxygenated" for up to several hours in vivo, within the lungs, where it directly participated in gas exchange. This was surprisingly accomplished using a conventional gas ventilator.

Briefly stated, the subject method of maintaining respiratory gas exchange includes the steps of: introducing into the pulmonary air passages of a mammalian host a volume of perfluorocarbon liquid substantially equivalent to (or less than) the normal pulmonary functional residual capacity of the host; maintaining respiratory gas exchange in the perfluorocarbon liquid-laden pulmonary air passages by continuous positive pressure breathing for a treatment period of time (e.g., up to an hour or more); and thereafter allowing evaporation of the perfluorocarbon liquid from the pulmonary air passages.

This perfluorocarbon associated gas exchange method provides advantages of both liquid ventilation and of continuous positive pressure breathing. Liquid ventilation with oxygenated perfluorocarbon eliminates surface tension due to pulmonary air/fluid interfaces, and improves pulmonary function and gas exchange in surfactant deficiency. In liquid ventilation, perfluorocarbon is oxygenated, purged of carbon dioxide, and the fluid is cycled into and out of the lungs using an investigational device. In contrast, perfluorocarbon associated gas exchange uses a conventional gas ventilator as in continuous positive pressure breathing.

As described in detail below, in thirteen normal piglets a volume of perfluorocarbon equivalent to the normal functional residual capacity (30 ml/kg) was instilled into the trachea, left in situ, and volume-regulated gas ventilation ($FIO_2 = 1.0$) was resumed. For one hour, perfluorocarbon was continuously bubble-oxygenated within the lungs, where it directly participated in gas exchange. The results showed that arterial $PaO_2$ and $PaCO_2$ averaged $401 \pm 51$ and $40 \pm 4$ torr ($53.6 \pm 6.8$ and $5.3 \pm 0.5$ kPa). Peak airway pressure during perfluorocarbon associated gas exchange ($22 \pm 2$ cm $H_2O$ at 1 hour) and during continuous positive pressure breathing ($23 \pm 4$ cm $H_2O$) were nearly identical. Venous oxygen saturation and pH were normal ($73 \pm 8\%$ and $7.43 \pm 0.05$ at 1 hour). Perfluorocarbon associated gas exchange was uniformly well tolerated, and its efficiency approached that of continuous positive pressure breathing. These results indicate that applications of perfluorocarbon breathing technology to lung disease are no longer limited by the state of existing instrumentation or the constraints associated with tidal liquid flow.

In this disclosure, by "method of maintaining respiratory gas exchange" is meant the means by which arterial $pO_2$, pH, and $pCO_2$ are maintained as close to normal as possible. This signifies adequate $O_2$ and $CO_2$ exchange in tissues throughout the body. The first objective of perfluorocarbon associated gas exchange is the assurance of such adequate gas exchange. The patient's underlying illness may then resolve without needless morbidity or mortality. In supporting gas exchange, arterial $pO_2$ is preferably maintained above 80 torr, and arterial $pCO_2$ is preferably maintained below 60 torr. Clearly, the closer the achieved values are to normal ($pO_2 = 100$, $pCO_2 = 40$), the more satisfactory the clinical situation. In neonates, excessively high $pO_2$ may cause retrolental fibroplasia and blindness, and so during perfluorocarbon associated gas exchange, as during conventional continuous positive pressure breathing, oxygen fraction may be reduced to prevent excessive oxygen tensions.

By "pulmonary air passages" is meant the pulmonary channels, spaces or volumes in the trachea, left and right bronchi, bronchiolus, and alveoli of the lungs that are normally occupied by air.

By "mammalian host" is meant to include humans, and, for research and veterinary purposes, premature lamb, piglet, rabbit, cat, dog, and others.

By "perfluorocarbon liquid" is meant to include any fluorinated carbon compound with appropriate physical properties for supporting (a) bubble-oxygenation (see below) during the inspiration phase of the PAGE cycle, and (b) minimal foaming and resultant liquid loss during the expiration phase. These requirements are generally met by perfluorocarbons having low viscosity, low surface tension, and low vapor pressure. A high solubility for $O_2$ is, of course, also required. The "perfluorocarbon liquid" may be made up only of atoms of carbon and fluorine, or may be a fluorochemical having atoms, e.g., bromine, other than carbon and fluorine. Representative perfluorocarbon liquids for use in perfluorocarbon associated gas exchange include FC-75, FC-77, RM-101, Hostinert 130, APF-145, APF-140, APF-125, perfluorodecalin, perfluorooctylbromide, perfluorobutyltetrahydrofuran, perfluoropropyltetrahydropyran, dimethyladamantane, trimethylbicyclononane, and mixtures thereof. Preferred perfluorocarbons are characterized by having: (a) an average molecular weight in range of from about 350 to about 570; (b) viscosity less than about 5 centipoise at 25° C.; (c) boiling point greater than about 55° C.; (d) vapor pressure in the range from about 5 to about 75 torr, and more preferably from about 5 to about 50 torr, at 25° C.; (e) density in the range of about 1.6 to about 2.0 $gm/cm^3$; and, (f) surface tensions (with air) of about 12 to about 20 dyne/cm.

The perfluorocarbon liquid is typically introduced into the pulmonary air passages after a period of at least ten to fifteen minutes of pure oxygen breathing. The perfluorocarbon may be conventionally introduced by simply injecting the liquid into the endotracheal tube between breaths, or by delivering the liquid under pressure, as is done during liquid breathing.

The volume of perfluorocarbon liquid introduced into the pulmonary air passages should preferably be substantially equivalent to the normal pulmonary functional residual capacity (FRC) of the host. By "pulmonary functional residual capacity" is meant the volume of space in the pulmonary air passages at the end of expiration. This FRC volume may change as the lung expands during the course of perfluorocarbon associated gas exchange. Filling the functional residual capacity with perfluorocarbon: (a) maintains functional residual capacity and prevents surface tension-induced alveolar closure during expiration; (b) obviates the need for alveolar air participation in gas exchange during expiration by purging of carbon dioxide and "bubble-oxygenating" an alveolar perfluorocarbon reservoir; (c) provides a low surface tension medium for bubble formation and bubble expansion throughout inspiration; and (d) reduces surface tension along much of the alveolar surface, where perfluorocarbon lies against the alveolar lining. By not exceeding the patient's FRC, the barotrauma associated with prior liquid breathing techniques is avoided, and adequate gas exchange via bubble-oxygenation is assured. PAGE treatments based on delivering volumes of perfluorocarbon liquid less than one FRC (e.g., ¾ FRC or ½ FRC) are also contemplated by this disclosure. Unilateral (one lung) or local (lobar, segmental) PAGE treatments may also be employed, e.g., for PAGE-mediated drug delivery to specific parts of the patient's pulmonary air passages.

Pursuant to this disclosure, respiratory gas exchange is maintained in such perfluorocarbon liquid-laden pulmonary air passages by continuous positive pressure breathing using a conventional ventilator. By "continuous positive pressure breathing" is meant positive pressure mechanical ventilation, often with positive end-expiratory pressure, and may be accomplished by any standard positive pressure ventilator. Either volume-regulated, time-cycled respirators or pressure-limited, time-cycled respirators are suitable. Such ventilators are commercially available. Representative models and manufacturers include: Servo 900C (Siemens Elema, Shaumburg, Ill.); Infant Star (Star Products, San Diego, Calif.); Bear 1, 2, 3 (Bear Medical, Bowins, Calif.); Baby Bird 2 (Bird Corp., Calif.); Healthdyne Infant Ventilator; Airshields; etc. As discussed below, the combination of bubble-oxygenation, gas defusion from perfluorocarbon to alveolar vessels, and ventilation/perfusion matching during perfluorocarbon associated gas exchange was not appreciably less efficient than was gas exchange during continuous positive pressure breathing. By "bubble-oxygenation" is meant intimate exposure of liquid to bubbles of gas such that bubbles and liquid equilibrate. This condition oxygenates the liquid and purges it of carbon dioxide. In inspiration, a volume of air is forced into the lungs and divided into small aliquots by the branching of the airway, so that bubbles form substantially uniformly throughout the lungs in the millions of terminal alveoli.

Following the perfluorocarbon associated gas exchange regimen, the perfluorocarbon liquid is removed from the pulmonary air passages. The preferred technique for this particular purpose is to simply permit the perfluorocarbon to evaporate from the pulmonary air passages. Continuation of gas ventilation without instillation of additional perfluorocarbon (to maintain the functional residual capacity) results in substantially complete evaporation from the lungs in a time period (determined by the vapor pressure of the perfluorocarbon) on the order of hours.

For certain purposes (discussed below), liquid breaths of the perfluorocarbon may be periodically cycled into and out of the pulmonary air passages during the treatment period.

Considered in more detail, the subject perfluorocarbon associated gas exchange (PAGE) method, by obviating the needs for continuous tidal liquid flow and extracorporeal gas exchange, can be advantageously implemented using a much simplified respiratory support system.

Figure 1:
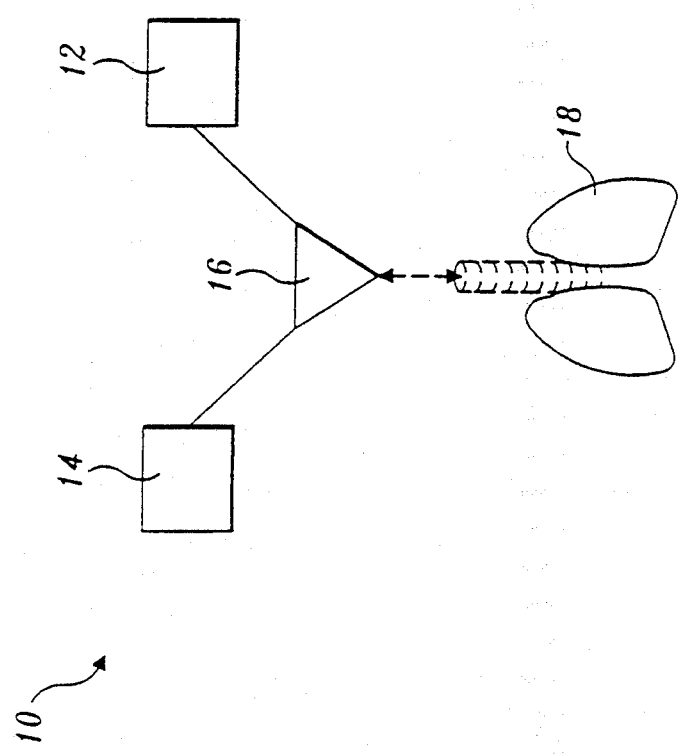
FIG. 1 shows an exemplary system for carrying out the subject perfluorocarbon associated gas exchange method.

Referring to FIG. 1, an exemplary system 10 for this purpose includes a conventional gas ventilator 12, a PAGE device 14 for handling and processing the perfluorocarbon liquid, and a PAGE adapter 16 that provides fluid communication with the patient's pulmonary air passages 18. The PAGE device 14 basically instills the predetermined volume of perfluorocarbon through the PAGE adapter 16 into the patient's pulmonary air passages 18; the gas ventilator 12 provides ventilation of the perfluorocarbon-laden pulmonary air passages 18; and the PAGE adapter 16 provides a means of cycling between these liquid movement and gas ventilation phases of the treatment.

The PAGE device 14 functions to: (a) cycle perfluorocarbon into (and, if desired, out of) the lungs; (b) reestablish the proper volume of liquid functional residual capacity, e.g., at the end of each liquid cycled breath, during the perfluorocarbon associated gas exchange treatment; (c) control the process of coordinating PAGE device-controlled liquid breaths and gas-ventilator breaths; (d) oxygenate the perfluorocarbon and purge it of carbon dioxide before instilling the liquid into the pulmonary air passages 18; (e) perform the process of initially loading the pulmonary air passages 18 with perfluorocarbon, if so desired; (f) periodcally cleanse the perfluorocarbon of debris prior to recycling the liquid into the pulmonary air passages 18; (g) regulate perfluorocarbon temperature; (h) measure pressures and flows within the perfluorocarbon conduits of the PAGE device 14 and/or PAGE adapter 16; (i)receive and process various physiologic measurements; and (j) manage input from its operating console and output of its computer.

The PAGE adapter 16 functions to: (a) mechanically, under control of the PAGE device 14, perform the process of coordinating liquid-cycled (PAGE device) and gas-ventilator (perfluorocarbon associated gas exchange) breaths; (b) mechanically permit the PAGE device 14 to restore appropriate liquid functional residual capacity within the pulmonary air passages 18; and (c) physically link the two types of fluid delivery devices (the gas ventilator 12 and the PAGE liquid-delivery device 14) for optimal application of the subject perfluorocarbon associated gas exchange method.

The use of such a system 10 (PAGE device 14, PAGE adapter 16, and gas ventilator 12) is exemplified by the following treatment protocol: In appropriate patients, perfluorocarbon is instilled into the lung, either as described in the following Examples, or by use of a PAGE ,device 14 and PAGE adapter 16. Perfluorocarbon associated gas exchange is generally the primary method of supporting respiratory gas exchange during the treatment period. The gas ventilator 12 delivers tidal volumes of gas to the perfluorocarbon-laden lungs 18 as determined by the operating console of the gas ventilator 12. The gas oxygenates the perfluorocarbon and purges the liquid of carbon dioxide in situ, in vivo, within the pulmonary air passages 18, with every breath. This process is performed repeatedly.

Referring to FIG. 2, at intervals set on the operating console of the PAGE device 14, a valve 20 in the PAGE adapter 16 is flipped to disengage the gas ventilator 12 from the endotracheal tube 22 leading to the patient's pulmonary air passages 18, and to open a gas ventilator port 24 to the ambient atmosphere. This valve 20 simultaneously establishes fluid communication between the PAGE device 14 and the patient's air passages 18. One or more PAGE device-controlled liquid breath(s) are then instilled and withdrawn to accomplish one or more of the above-stated purposes of the PAGE device 14. The valve 20 of the PAGE adapter 16 is then flipped (by a signal from the PAGE device 14) to disengage the PAGE device 16 and to reengage the gas ventilator 12 for continued support of gas exchange. This cycle (of engaging the pulmonary air passages 18 to the gas ventilator 12, then the PAGE device 14, then the gas ventilator 12) may be repeated as sequenced by a computer in the PAGE device 14, in response to instructions from its operating console.

The illustrated PAGE adapter 16 is a Y-Shaped conduit for perfluorocarbon, air, ventilator gas, and expired gas. The adapter 16 has two upper limbs (a PAGE device conduit 26 and a gas ventilator conduit 28), a low dead-space common chamber 30, a flap valve 20 with twist stem 32, and a switch mechanism (not shown) that rotates the twist stem 32 to reciprocally operate the valve 20.

The gas ventilator conduit 28 is typically short (to minimize dead space) and establishes gaseous communication between the ventilator 12 and the common chamber 30. This gas conduit 28 may contain an aperture or port 24 that is reversibly sealed, e.g., by a pad 34 on the reciprocal end of flap valve 20, when the valve 20 engages the gas ventilator 12, but open when the valve 20 engages the PAGE device 14.

The common chamber 30 typically has low dead space and fits the distal hub 36 of the patient's endotracheal tube 22. The common chamber 30 has two other outlets, one 36 to the gas ventilator conduit 28, and the other 38 to the PAGE device conduit 26. The common chamber 30 reversibly communicates with either this gas outlet 36 or this liquid outlet 38 by means of valve 20. This valve 20 can take the form, as shown here, of a flap valve 20 mounted on an axle or twist stem 32. Turning the stem 32 rotates the valve 20 to engage the orifice 36, 38 of one conduit 28 or the other 26.

The PAGE device conduit 26 contains three channels, each of which courses from the orifice 38 of the chamber 30 to a port on the PAGE device 14. These channels direct flow of: (a) air via channel 40 from the PAGE device 14 to the common chamber 30; (b) perfluorocarbon inflow (to the patient) via channel 42 from the PAGE device 14 to the common chamber 30; and (c) perfluorocarbon outflow via channel 44 from the common chamber 30 to the PAGE device 14.

Figure 3A:
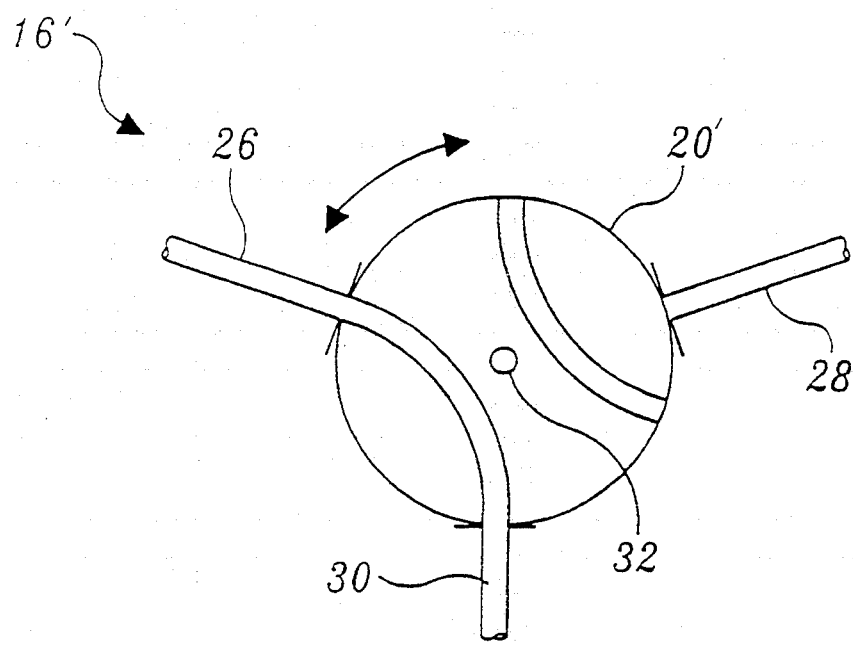
FIGS. 3A and 3B show other exemplary adapters for switching between perfluorocarbon associated gas exchange and continuous positive pressure breathing.
Figure 3B:
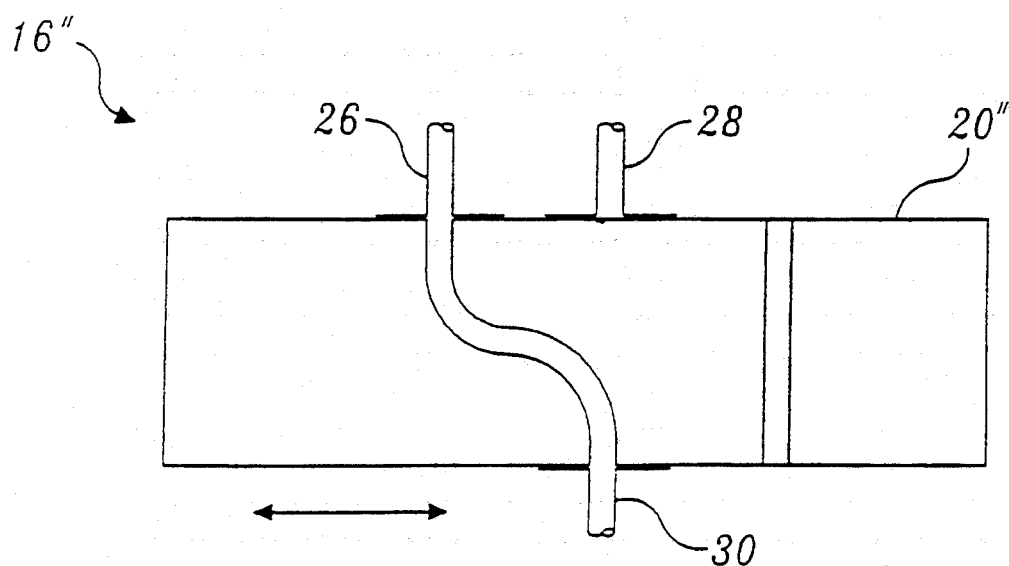

It should be understood that the above-described PAGE device 16 is merely illustrative. The fluid-control valve means 20, for example, can alternatively take the form of a conventional rotatable channel valve 20' as shown in FIG. 3A, or a sliding piston channel valve 20" as shown in FIG. 3B may be employed.

Figure 4:
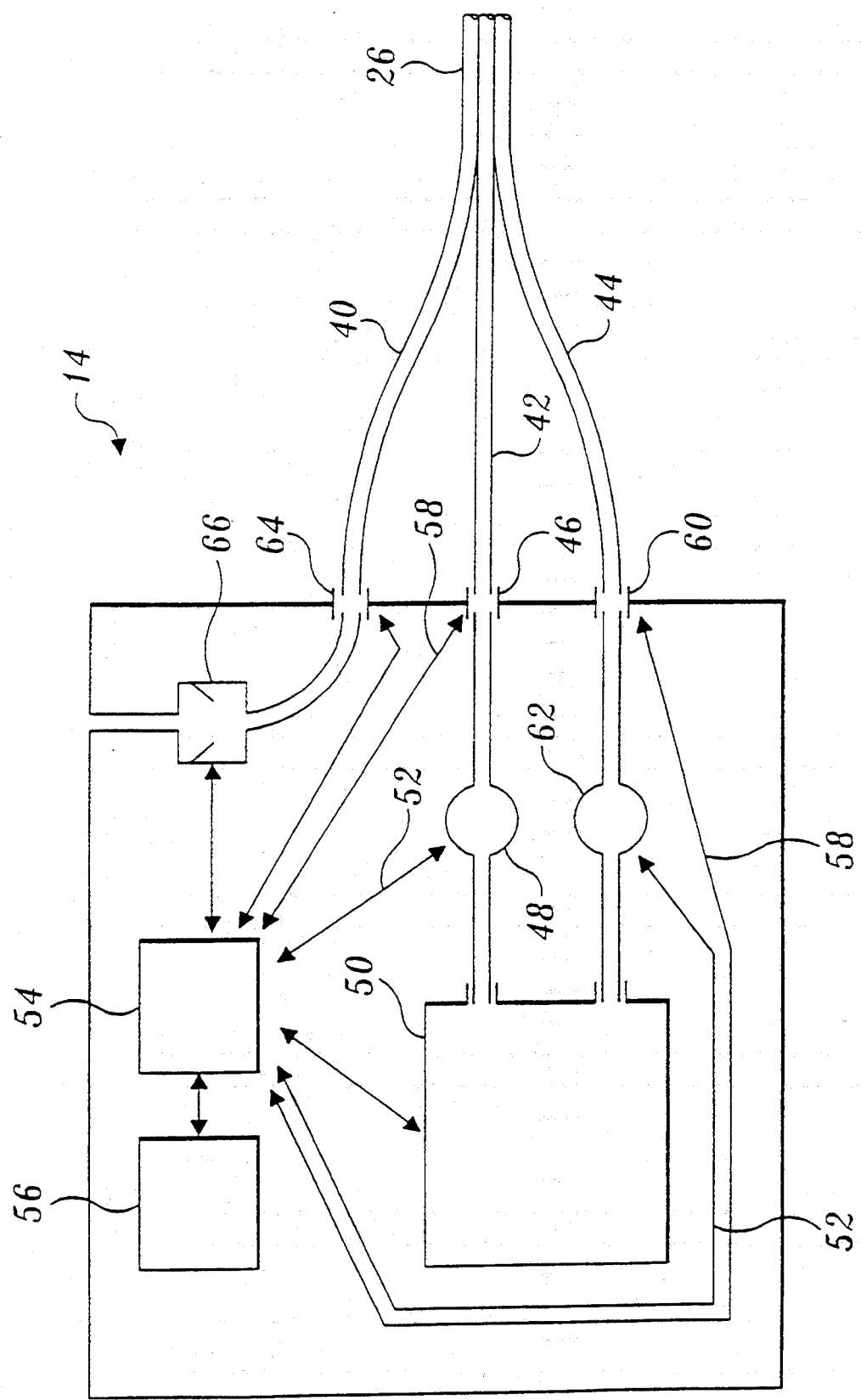
FIG. 4 shows an exemplary PAGE device for maintaining the liquid functional residual capacity during the PAGE treatment regimen.

Referring to FIG. 4, an exemplary PAGE device 14 has three ports to receive the distal ends of the channels 40, 42, 44 from the PAGE-adapter conduit 26, pumps and valves to control fluid flow through the channels 40, 42, 44, a computer with clock, a reservoir with connectors and apparatus for processing perfluorocarbon, an oxygen (or blender) source port, an operating console, a control cable to operate the PAGE-adapter valve 20, input and output channels, and support electronics to gather data for the computer's use and to drive components of the system 10.

One port 46 couples the PAGE device 14 to the inflow channel 42 that carries perfluorocarbon from the PAGE device 14 to the common chamber 30 of the PAGE adapter 16. This port 46 is linked by a pump 48 to the perfluorocarbon reservoir 50. The pump 48 is controlled via an output link 52 by the computer 54 as directed by the operating console 56. This inflow pump 48 delivers a predetermined volume of perfluorocarbon to the port 46 over a predetermined period of time. Pressure at this port is measured and continuously monitored by an input link 58 to the computer.

A second port 60 couples the outflow conduit 44 from the common chamber 30 to the perfluorocarbon reservoir 50 in the PAGE device 14, again by way of a pure 62. Perfluorocarbon returns to the reservoir 50 through this port 60. The associated pump 62 is controlled via an output link 52 by the computer 54, as directed by the operating console 56, in order to return a predetermined volume of perfluorocarbon to the port 60 over a predetermined period of time. Pressure at this port 60 is measured and continuously monitored by an input link 58 to the computer.

The third port 64 couples the air channel 40 between the common chamber 30 to the PAGE device 14. This port 64 allows air to flow into the common chamber 30 during a predetermined time segment of the PAGE device cycle. The computer 54 sets the pressure below which air is allowed to pass through a one-way air valve 66 through the port 64 and into the channel 40.

Coordination of the three ports 46, 60, 64 and their associated pumps 48, 62 and valve 66 permits the PAGE device 14 to restore liquid functional residual capacity at the end of the liquid cycled breath. When the air valve 66 is closed, the outflow pump 62 removes perfluorocarbon liquid from the pulmonary air passages 18 by negative pressure (as preset by the console 56 and computer 54). When air is free to pass through port 64 into the common chamber 30 of the PAGE adapter 16, the PAGE device 14 will only remove any perfluorocarbon that wells up into the common chamber 30 by passive recoil of the lung and thorax. For example:

| | Clock Time On (air valve open) | Clock Time Off (air valve closed) | Setting |
|---|---|---|---|
| Inflow pump 48 | 0 sec | 6 sec | 10 ml/sec |
| Outflow pump 62 | 6 sec | 16 sec | 10 ml/sec |
| Air valve 66 | 10 sec | 16 sec | atmospheric pressure |

In this representative example, pump 48 associated with inflow port 46 delivers 60 ml of perfluorocarbon to the pulmonary air passages 18. Pump 62 associated with outflow port 60 removes 40 ml of perfluorocarbon from the pulmonary passages 18 between 6 and 10 seconds. Recoil of the lung delivers the difference between functional residual capacity (at atmospheric pressure) and lung volume at clock time 10 seconds to the common chamber 30 over the next 6 seconds. That volume is removed by the outflow pump 62 at the rate at which the liquid is delivered by recoil, because pump 62 cannot create a vacuum to withdraw the liquid faster, at the 10 ml/sec rate set for the pump 62, with the air valve 66 open. The difference between set pump flow rate and the rate at which perfluorocarbon is delivered to the common chamber 30 by recoil of the lung is made up by air inflow at set (atmospheric) pressure.

A pneumotachometer (not shown) may be placed in the air port 64 to ascertain when functional residual capacity has been reached. With the air valve 66 open, when there is no further lung recoil, the rate set for pump 62 would equal the flow into the air port 64. In this manner, the PAGE device 14 can readily monitor and restore functional residual capacity (FRC), whereas this is a complex problem in liquid breathing because of the large volumes of liquid delivered to and removed from the lungs every minute. The PAGE device 14 notably has less flow to deal with, less volume to purify, less liquid to heat, and does not require continuous weighing of the patient to monitor FRC.

The computer 54 of the PAGE device 14 collects the following input: (a) settings for timing and flow rates for the pumps and valves of the three ports as set on the operation console; (b) cycle timing for the PAGE-adapter valve 20 as set on the operating console; (c) input from pressure and flow sensors related to the three ports; (d) physiologic measurement signals such as esophageal pressure; and (e) input from sensors related to reservoir activities.

Computer output functions to: (a) time and operate the pumps and air valve within the PAGE device 14; (b) time and operate the valve 20 of the PAGE adapter 16; and (c) report all measurements and computations to meters on the operating console and, by auxiliary and output data ports (not shown), to hard copy recorders or external computers remote from the device 14.

The reservoir 50 functions to: store perfluorocarbon, bubble oxygenate it to preselected oxygen fraction, regulate its temperature over the physiologic or therapeutic range desired, purify and cleanse the perfluorocarbon of debris, and track loss of liquid volume from the system.

The operating console 56 functions to: (a) allow the operator to set parameters for operation of the PAGE device 14 and PAGE adapter 16; (b) display significant output from the computer for interpretation and human response; and (c) sound alarms when measured parameters exceed the limits set for operation of the PAGE device 14.

To accomplish perfluorocarbon associated gas exchange using a conventional gas ventilator 12, a PAGE adapter 16, and a PAGE device 14, the following operational range of parameters are considered to be representative. The gas ventilator 12 is engaged to the patient as much as 95% of the time, or as little as 75% of the time. The gas ventilator 12 might operate at as few as 5 breaths per minute, or as many as 40 breaths per minute. Peak pressure would range from as low as 15 cm $H_2O$ to as high as 60 cm $H_2O$ (25 cm $H_2O$ would probably be ideal). Oxygen fraction of the PAGE device 14 or ventilator 12 might be as low as 21%, or as high as 100%. Tidal volumes of conventional ventilator breaths delivered to the endotracheal tube 22 might be as small as 6 ml/breath, or as large as 18 ml/breath. Positive end-expiratory pressure (PEEP) might or might not be required on the conventional ventilator 12. Ideally, no more than 5 cm $H_2O$ PEEP will be required, but PEEP may be as high as 20 cm $H_2O$ at times during the perfluorocarbon associated gas exchange treatment. The PAGE device 14 might be engaged to the patient for single liquid breaths, or for as many as 3 or 4 such breaths in sequence. The air valve 66 of the PAGE device 14 may open at ambient pressure, or at 10-20 cm $H_2O$ below ambient.

The disclosed system 10 may also be provided with condensation means (not shown) to capture and recirculate perfluorocarbon vapors. While perfluorocarbon liquids are indeed biologically inert and nontoxic in the pure form that would be appropriate for direct infusion into the pulmonary air passages, the existence of perfluorocarbon vapors in the surrounding environment is, paradoxically, hazardous. This fact, while ignored through most of the research history of liquid ventilation, is profoundly relevant to the practice of PAGE therapy, since evaporative perfluorocarbon losses may be quite high (10-20% of functional residual capacity per hour could translate into environmental vapor losses of about 400-800 gm/hour for adult PAGE treatments).

The reason for perfluorocarbon vapor hazard is that the vapors can decompose into hazardous byproducts upon contact with common sources of heat, e.g., hot light sources, burning cigarettes, open flames, ovens, glowing electrical elements, electrical arcs (e.g., in common motors), electrosurgical devices, surgical lazers, and so on. The most typical decomposition products are perfluoroisobutylene (PFIB) and hydrogen fluoride (HF). The highly corrosive and toxic nature of HF is well known. Since PFIB boils at 7° C. it will exist as a gas mixed with the ambient air in the clinical environment. Inhaling PFIB in concentrations as low as about 0.5 parts-per-million for even a few hours can be fatal.

Even where adequate room air recirculation and ventilation exist to keep toxic concentrations around the PAGE process fairly low, the very creation of potentially toxic emissions in the local environment is cause for concern. Additionally, based on the extremely high expense of perfluorocarbon liquids, extensive patient PAGE treatments (e.g., greater than a few hours) will warrant the recapture of the evaporated perfluorocarbon liquid and recycled use in the same patient during the treatment. Thus, there are safety and economic motivations for the condensation recovery of evaporated perfluorocarbon loss both from the PAGE device and from the lungs while being ventilated with gas tidal flows. This condensation function, as well as the additional function of reintroducing the condensed perfluorocarbon vapors back into the PAGE device, can be carried out by an effluent vapor condensation module. This device takes in both effluent gas/vapor mixture from the PAGE device and expiratory gas/vapor flow from the patient while being ventilated by the gas ventilator (at the point before this mixture vents to the ambient atmosphere). The expiratory mixture is pumped into the module from either (a) the outlet of a connector near the proximal end of the endotracheal tube in passive expiration use, or (b) the outlet of expiratory flow from the gas ventilator (in cases where expiratory gas is actually drawn through the gas ventilator itself). The condensation module may be integrated into the PAGE device 14 or may be employed as an attachment to the gas ventilator 12.

The condensation module connected to a patient's expiration tube (for passive expiration) will likely be required to take flow from a proximal point in the expiratory flow which is near atmospheric pressure or at slightly positive pressure. The patient should not be "loaded" in the sense that the pumping of the gas/vapor mixture creates a significant series airway resistance on expiration. As such, the module can be required to "draw" mixture from a vented plenum (which receives the expiratory mixture just outside the patient) near atmospheric pressure through a cheek valve. The drawing or suction of this flow may be provided by a vacuum pump.

To meet the requirements for patient perfluorocarbon reuse for extended treatments, the condensation module pumps perfluorocarbon liquid flow to the PAGE-device reservoir 50 either (a) periodically at fixed time intervals, (b) on the basis of sensed minimum accumulated volumes in the modules perfluorocarbon storage reservoir, or (c) by continuously pumping. Such perfluorocarbon return pumping is controlled by the PAGE-device computer 54.

The subject PAGE method, by simplifying the mechanisms of oxygenation and carbon dioxide clearance, provides a preferred means of gas exchange for respiratory applications of perfluorocarbon technology. The PAGE method reduces the matter of "ventilation" to one of air movement, whereas prior liquid breathing techniques have been hampered by the need to move relatively large volumes of liquid into and out of the lungs. Traditional liquid breathing requires the movement of such large volumes of fluid per minute that it becomes necessary to force fluid into or out of the lung, at relatively high airway pressure, almost continuously. This reduces the margin of safety of conventional liquid breathing, and limits its flexibility. It exposes the proximal airway to high inspiratory pressures, even though distal airways and alveoli are exposed to far lower pressure. The disclosed PAGE method may reduce the risk of these high proximal airway pressures, greatly increase the flexibility of liquid breathing technology, and simplify the problem of regulating pulmonary functional residual capacity.

By simplifying the problem of gas exchange during respiratory applications of perfluorocarbon breathing technology, the PAGE method readily permits more efficient, less complex apparatus for the processes of recycling perfluorocarbon, cleansing it of debris, and regulating its temperature.

The process of PAGE, permissibly practiced with a PAGE adapter 16 and a PAGE device 14, also modifies the priorities that determine selection of the best liquids for liquid breathing techniques. The PAGE process may lend itself to respiratory applications of classes of liquids other than perfluorocarbons. Fluids can now be selected more on the basis of surface tension and viscosity for transmission of gas bubbles, and less on the basis of solubilities for oxygen and carbon dioxide. Chemicals poorly suited to conventional liquid breathing may prove effective vehicles for PAGE. For example, low water content (e.g., from several percent up to about 25% $H_2O$) perfluorocarbon emulsions may be highly desirable for PAGE as vehicles for lavage of debris and delivery of drugs, though they might be unsuitable for gas exchange by conventional liquid breathing. The critical factor, when such weak water or saline emulsions are employed, is to assure that the perfluorocarbon is on the outside of the aqueous phase; otherwise, unacceptable foaming and liquid loss during expiration will likely result.

The subject perfluorocarbon associated gas exchange method is useful for treating various disorders and diseases of the pulmonary air passages. In particular, respiratory distress syndromes associated with surfactant deficiency or dysfunction are functionally made less severe throughout the duration of perfluorocarbon associated gas exchange, by limiting the maximum surface tension that must be overcome in ventilating the lung to that of the perfluorocarbon itself. Other clinical applications of the perfluorocarbon associated gas exchange method are discussed below.

Thus, PAGE is a particularly useful way to ventilate the lung with surfactant deficiency (respiratory distress syndrome of prematurity), and the lung with surfactant dysfunction and capillary leak syndrome (e.g., Adult Respiratory Distress Syndrome (ARDS), meconium aspiration syndrome, and various forms of acute lung injury).

Prophylactic use of PAGE is also contemplated for preventing or minimizing lung dysfunction associated with, e.g., ARDS, immune-mediated lung injury, irritant injuries to the lung, cytiokine-mediated or endotoxin-mediated injuries, and other sources of lung injury.

PAGE, by simplifying gas exchange during liquid breathing, should make it possible to use perfluorocarbon products as lavage media to cleanse the lung of debris (e.g., meconium aspiration syndrome, alveolar proteinosis, life-threatening asthma, cystic fibrosis, and other aspiration syndromes).

PAGE should make it possible to keep the lung full of low surface tension perfluorocarbon liquid for a prolonged period of time and thereby permit the use of perfluorocarbons to prevent or reduce the severity of lung injury and lung dysfunction in patients prone to ARDS. Capillary leak is a function of surface tension at the alveolar lining, and could be significantly reduced in these patients by constant presence of perfluorocarbon. Though the surface tension of the perfluorocarbon itself may be between 10 and 20 dynes/cm, that of the alveolar lining/perfluorocarbon interface is much closer to 1 dyne/cm, and may be lower than the normal surface tension of the alveolar lining even in the absence of surfactant.

PAGE should provide advantages over conventional gas ventilation in resuscitation from cardiopulmonary arrest. The noncompressible nature of liquid perfluorocarbon may enhance the transmission of precordial pressure to the arrested heart during CPR.

PAGE should provide advantages over standard therapy for resuscitation after cold-water drowning and other states characterized by hypothermia as well as cardiac arrest. The perfluorocarbon can be warmed, using the PAGE device 14, and, during PAGE, used to rewarm the mediastinum and central blood volume, thereby obviating the need for ECMO or cardiac bypass in such cases. Continuous manipulation of perfluorocarbon, mediastinum, and heart temperature may be accomplished using the PAGE device 14.

The PAGE method and system 10 may also find applications for cooling and/or rewarming in conjunction with operative hypothermia. This may find special applications in cardiac surgery.

The PAGE method and system 10 may find applications for cooling and/or rewarming in conjunction with the management of head trauma or brain injury.

PAGE should also provide an effective means for removal of nitrogen bubbles from blood after acute decompression from depth, and so will find applications in treatment or prevention of the "bends".

PAGE should provide a safe alternative to conventional liquid breathing, thereby assuring the safety of that technique (against the possibility of liquid breathing equipment failure). Use of the PAGE adapter 16 will enhance the safety of conventional liquid breathing by assuring rapid institution of PAGE should equipment failure occur during conventional liquid breathing.

PAGE, because it predominantly involves tidal flow of gas rather than liquid, should prove effective in diseases characterized by combined airway obstruction and elevated alveolar surface tension. An example of such a disease is ARDS.

The PAGE adapter 16 will facilitate the intermittent use of conventional liquid breathing techniques, by making it possible to safely and conveniently execute the transition between conventional liquid breathing and the gas ventilation of PAGE.

The PAGE device 14 and PAGE adapter 16, together, serve to facilitate the consistent maintenance of an optimal pulmonary functional residual capacity. This enhances the safety of respiratory applications of perfluorocarbon breathing technology, and greatly simplifies the safe execution of the process of conventional liquid breathing.

PAGE should facilitate mechanical ventilation in the presence of cardiogenic pulmonary edema. The subject method may also reduce the rate of accumulation of lung water during cardiogenic pulmonary edema.

PAGE, preferably practiced with the disclosed system 10, may provide a means of "cardiac augmentation" by reduction of cardiac afterload in patients with congestly cardiac failure. Transmission of the weight of perfluorocarbon to the cardiac fossa may, during PAGE, reduce left ventricular afterload.

PAGE may prove useful in the reexpansion of atelectatic lung segments. It may have special value in the reinflation of lung segments that collapse during Extracorporeal Membrane Oxygenation (ECMO). PAGE may, in fact, prove superior to conventional gas ventilation in the long-term support of the lungs during ECMO, as it may reduce the tendency to further barotrauma and maintain alveolar and airway pathway during lung healing.

The long-term presence of perfluorocarbons within the airways and alveoli during PAGE may alter the healing process of the injured or infected lung, and prevent progression to airway obliteration.

The long-term presence of perfluorocarbons within the airways and alveoli made possible by the PAGE and system 10 may depress the inflammatory process, and thereby ameliorate the lung injury associated with immunologic and hypersensitivity lung disease.

PAGE may, by ameliorating stimuli to pulmonary vasoconstriction, prove to be an effective support modality for infants with persistent pulmonary hypertension of the neonate.

PAGE may, by providing a relatively static pool of pulmonary liquid, effectively distribute and leave *in situ* various drugs and pharmacologic or diagnostic agents, including surfactant, mucolytics, and agents that alter bronchomotor tone. Representative agents for this purpose include vasoactive substances such as epinephrine and norepinephrine, proteolytic enzymes such as those used to break up blockages in cystic fibrosis, bronchodialators such as terbutaline and albuterol, steroids and other anti-inflammatory agents, chromalyn, chemotherapeutic or diagnostic antibody reagents, and so on.

PAGE may also, by promoting the even distribution of gas in the lung during inspiration, and by reducing the distending pressure required to ventilate lungs with high intrinsic surface tension, reduce the incidence of pulmonary barotrauma during mechanical ventilation.

The invention is described in additional detail by the following representative examples.

EXAMPLES

Methods and Materials

The following studies were approved by the Animal Care and Use Committee of the Children's Hospital of Pittsburgh. Care and handling of animals conformed to NIH guidelines.

Thirteen piglets, ages 3 to 21 days, and weighing $2.9 \pm 0.6$ kg, were anesthetized with alpha-chloralose (50 mg/kg) and paralyzed using metocurine iodide (0.3 mg/kg). Airways were secured by intubation followed by tracheostomy, and the trachea was tightly secured to the tracheostomy tube. Volume-controlled continuous positive pressure breathing was instituted using a commercially available ventilator (Servo 900C, Siemens Elema, Shaumburg, Ill.). Arterial and central venous catheters were placed by femoral cutdown for vascular pressure measurement and blood sampling. These measurements were interfaced to a fiber-optic recorder (PPG Biomedical, Pleasantville, N.Y.). Animals were studied supine and with chest closed.

During stabilization, dextran (Gentran, 5%) was administered in 5-ml/kg aliquots to achieve a right atrial pressure between 5 and 8 mm Hg. Minute ventilation was adjusted to obtain $PaCO_2$ between 30 and 45 torr (4 and 6 kPa) at respiratory rates of 18 to 25 breaths/minute. Inspiration was restricted to 25% of the respiratory cycle, and 2 to 5 cm $H_2O$ positive end-expiratory pressure was applied. Lungs were ventilated with oxygen ($FIO_2$ 1.0).

In five piglets, the pulmonary pressure/volume relationship was studied, before institution of perfluorocarbon associated gas exchange, over the range of lung volume associated with tidal breathing. Proximal airway pressure was measured continuously with a dry transducer. Continuous positive pressure breathing was discontinued. The thorax was allowed to assume passive functional residual capacity at ambient pressure. The lungs were then inflated with air in 10-ml aliquots to 15 to 25 ml/kg above functional residual capacity. The deflation limb of the pressure/volume curve was similarly determined by withdrawing 10-ml aliquots until airway pressure decreased below the ambient pressure.

In these same piglets, the expiratory flow/volume relationship was studied during continuous positive pressure breathing by interposing between the ventilator and the tracheostomy tube a pneumotachometer (Hans Rudolph, Kansas City, Mo.) interfaced to a respiratory integrator (Hewlett Packard, Waltham, Mass.). Flow and volume were recorded simultaneously during continuous positive pressure breathing for later construction of flow-volume and real-time volume curves.

All studies were performed using the perfluorocarbon FC77 (3M, St Paul, Minn.), known to have density 1.75 g/ml, viscosity of 0.66 centistokes, surface tension of 14 dynes/cm, vapor pressure of 75 torr (10 kPa), and solubilities for oxygen and carbon dioxide of 56 and 198 ml gas/100 ml perfluorocarbon at 1 atmosphere pressure, respectively (all at 37° C.). FC77 is immiscible in water and is closely related to other perfluorocarbons known to have negligible pulmonary absorption.

Once steady state was achieved during continuous positive pressure breathing, arterial and venous blood were sampled, ventilatory measurements were performed, and vascular pressures were recorded to obtain data tabulated below.

A volume of 30 ml/kg FC77, chosen to approximate the normal functional residual capacity, was preoxygenated at $FIO_2$ 1.0 and warmed to 37° C. and was then instilled into the trachea over 30 to 60 seconds. Gas ventilation of the perfluorocarbon-filled lung was then resumed ("perfluorocarbon associated gas exchange") using the same ventilator settings as those used during continuous positive pressure breathing.

Perfluorocarbon associated gas exchange was continued for 1 hour without changing ventilator settings. Over this period, 10 to 20 ml of FC77 was added to the lungs as needed to replace evaporative losses and compensate for changes in functional residual capacity, in order to maintain an expiratory meniscus of perfluorocarbon in the vertical outlet of the transparent tracheostomy tube at ambient pressure. At no time was perfluorocarbon drained from the lungs. No other drugs or fluids were administered. After 5, 15, 30, and 60 minutes of perfluorocarbon associated gas exchange, blood, respiratory, and hemodynamic measurements were repeated.

After 60 minutes of perfluorocarbon associated gas exchange, pressure/volume and flow/volume studies were repeated (as described above) in the same piglets studied before perfluorocarbon associated gas exchange to ascertain the effects of perfluorocarbon instillation on inflation and deflation of the lungs with gas. Perfluorocarbon was not drained prior to these measurements.

To study static pressure/volume relations after perfluorocarbon associated gas exchange, ventilation was interrupted. The perfluorocarbon-filled lung was allowed to assume its residual capacity at ambient pressure. No attempt was made to measure this functional residual capacity, nor was an effort made to assure that functional residual capacity of the perfluorocarbon-filled lung was comparable to functional residual capacity during continuous positive pressure breathing. A meniscus of perfluorocarbon was uniformly present in the transparent vertical shaft of the tracheostomy tube. Proximal airway pressure was again measured continuously with a dry transducer. The lungs were then inflated with air in 10-ml aliquots to a 15 to 25-ml/kg level above functional residual capacity. The deflation limb of the pressure/volume curve was similarly determined by withdrawing 10-ml aliquots of air until airway pressure fell below ambient.

To study the flow/volume relationship during perfluorocarbon associated gas exchange, air flow and volume were simultaneously recorded during perfluorocarbon associated gas exchange (as described above) for later construction of flow-volume and real-time volume curves.

Animals were then killed by bolus injection of potassium chloride. After death, selected piglets underwent sternotomy and resection of the right chest wall. Ventilation was resumed postmortem to observe the pattern of lung aeration during perfluorocarbon associated gas exchange.

Measurements repeated throughout the hour of perfluorocarbon associated gas exchange were compared to values measured during continuous positive pressure breathing using analysis of variance. Post hoc tests were subjected to a Newman-Keuls' correction for multiple comparisons.

Results

Instillation of FC77 was well tolerated in all animals with no apparent adverse respiratory or hemodynamic consequences, and perfluorocarbon associated gas exchange was instituted without adverse effects. No animal had an adverse event during perfluorocarbon associated gas exchange.

Gas exchange: Although there was a significant decline in $PO_2$ on institution of perfluorocarbon associated gas exchange, mean $PaCO_2$ remained stable (401±51 torr (53.6±6.8 kPa)) and arterial blood was fully saturated in every animal throughout the study period (Table 1). $PaCO_2$ was not significantly different during perfluorocarbon associated gas exchange from $PaCO_2$ measured during continuous positive pressure breathing. Alveolar-arterial oxygen difference during perfluorocarbon associated gas exchange (after correction for perfluorocarbon vapor pressure) and during continuous positive pressure breathing were comparable. Perfluorocarbon associated gas exchange did not cause metabolic acidosis.

and perfluorocarbon-filled lungs differ by about 4 cm H20 ($p<0.01$ by ANOVA at every level of lung inflation). Data is mean±sero.

Figure 6:
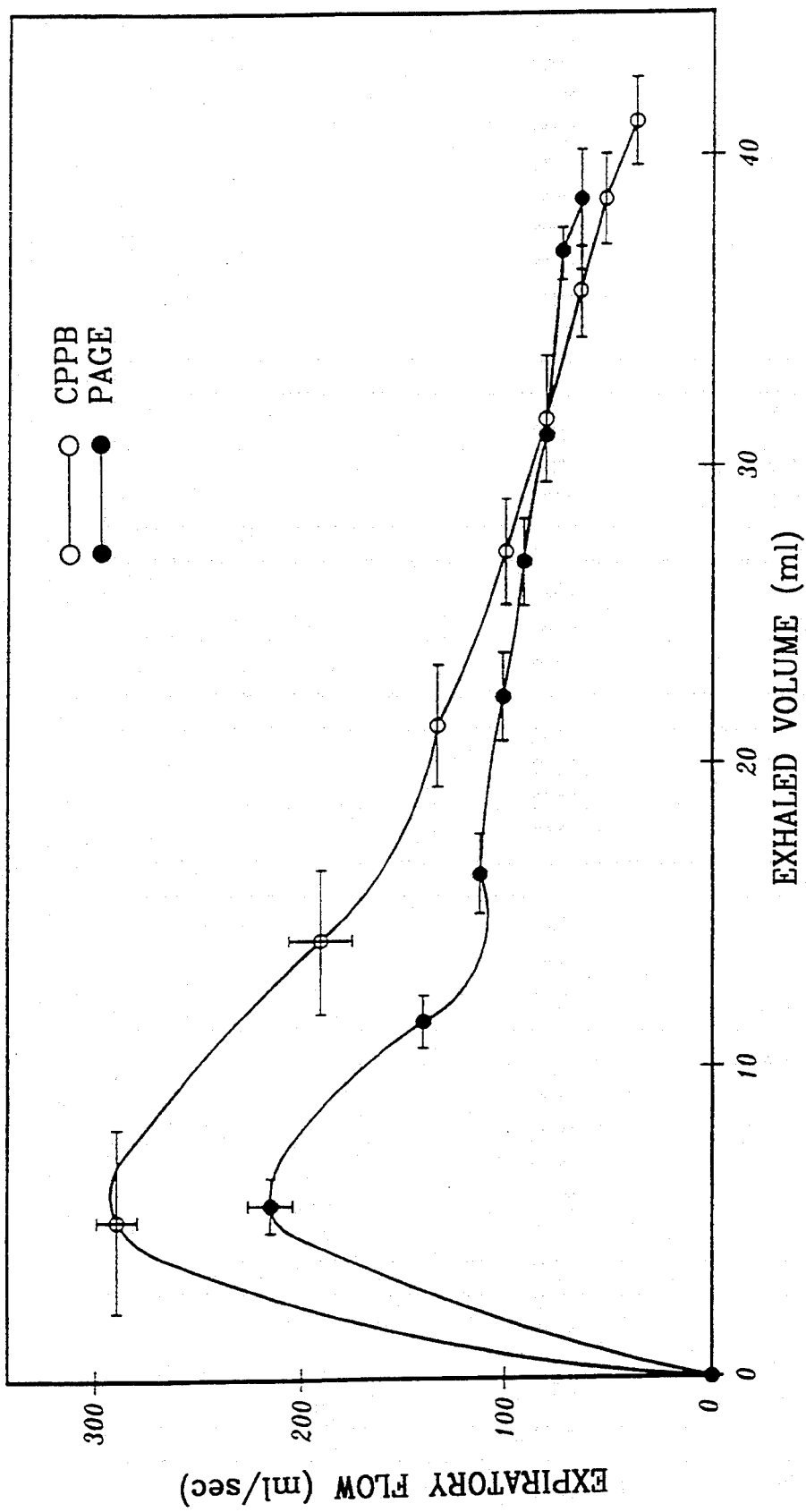
FIG. 6 compares the expiratory flow/volume relationship during continuous positive pressure breathing (open circles) and perfluorocarbon associated gas exchange (solid circles)

Expiratory flow: The expiratory flow/volume relationship was altered by instillation of perfluorocarbon, suggesting a modest increase in expiratory airway resistance (FIG. 6). Peak expiratory flow was decreased, but time to peak flow was unchanged, and pulmonary time constant was only slightly increased (from 0.19 to 0.23 sec). Exhalation was virtually complete in the first half-second of expiration (FIG. 7).

Referring to FIG. 6 in more detail, expiratory flow/volume relationships for perfluorocarbon associated gas exchange (PAGE) and continuous positive pressure breathing (CPPB) differ in that peak flow is attenuated by the modest elevation of airway resistance that occurs during perfluorocarbon associated gas exchange. Data is mean±sero.

Figure 7:
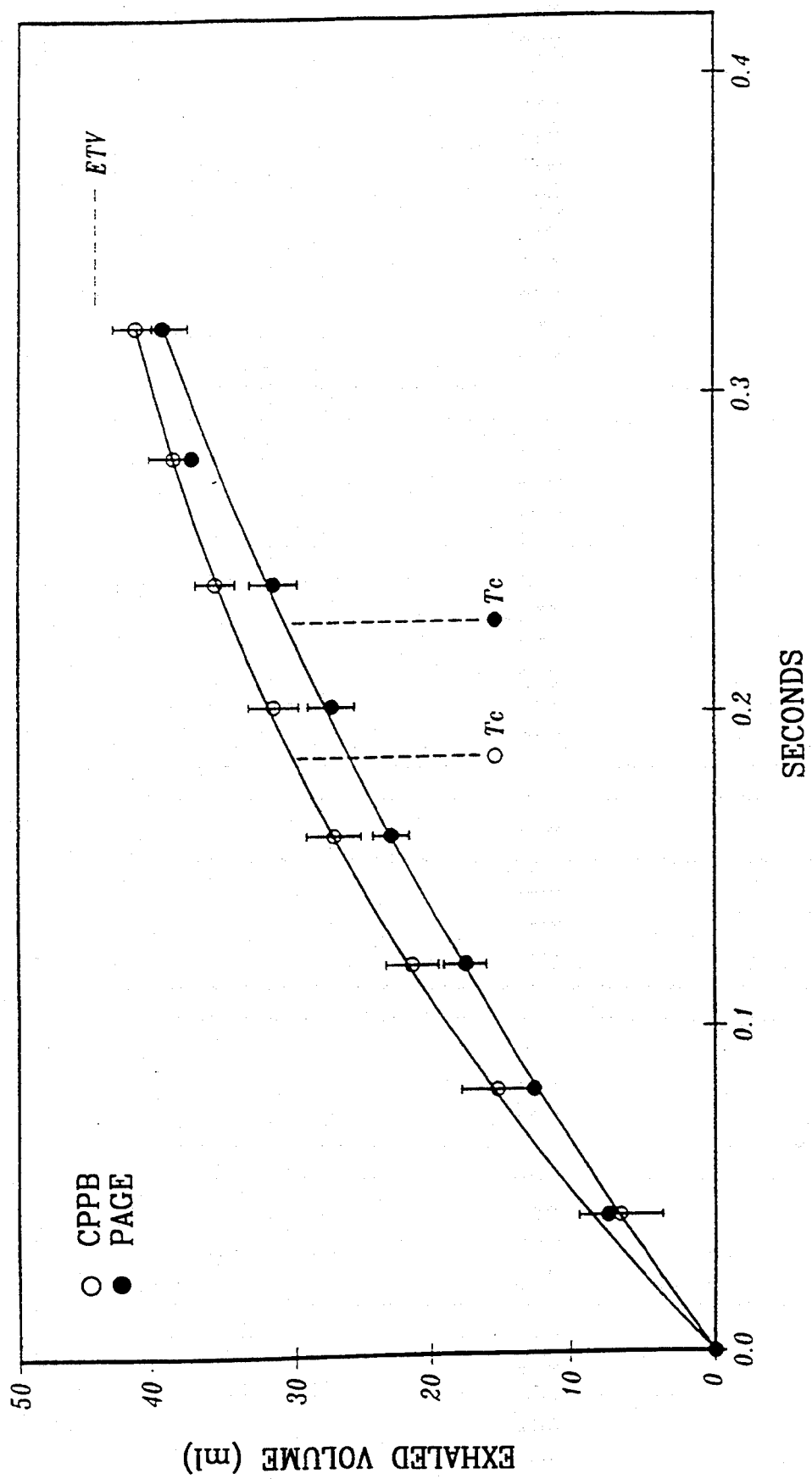
FIG. 7 compares time in expiration and exhaled volume during continuous positive pressure breathing (open circles) and perfluorocarbon associated gas exchange (solid circles)

Referring to FIG. 7, spontaneous exhalation against 2

TABLE 1

| | Gas exchange during CPPB and PAGE | | | | |
|---|---|---|---|---|---|
| | CPPB | Duration of PAGE (min) | | | |
| | | 5 | 15 | 30 | 60 |
| Ph | 7.42 ± .05 | 7.41 ± .04 | 7.42 ± .05 | 7.42 ± .05 | 7.43 ± .05 |
| paCO2, torr | 38 ± 6 | 40 ± 5 | 40 ± 4 | 40 ± 4 | 39 ± 4 |
| paCO2, kPa | 5.1 ± 0.8 | 5.3 ± 0.7 | 5.3 ± 0.5 | 5.3 ± 0.5 | 5.2 ± 0.5 |
| paO2, torr | 503 ± 64 | 429 ± 55** | 384 ± 38** | 392 ± 40** | 394 ± 62** |
| paO2, kPa | 67.2 ± 8.6 | 57.4 ± 7.4** | 51.3 ± 5.1** | 52.4 ± 5.3** | 52.7 ± 8.3** |
| HCO3— | 24 ± 2 | 25 ± 3 | 26 ± 2 | 25 ± 2 | 25 ± 2 |
| AaDO2, torr | 159 ± 61 | 157 ± 54 | 201 ± 37* | 194 ± 40 | 192 ± 61 |
| AaDO2, kPa | 21.3 ± 8.2 | 21.0 ± 7.2 | 26.9 ± 4.9 | 25.9 ± 5.3 | 25.7 ± 8.2 |

Gas exchange during PAGE was virtually as efficient as during CPPB. HCO3— is expressed in meq/l. All values are means ± SD. *$p < .05$ and **$p < .01$ vs values during CPPB by ANOVA with Newman Keuls correction for multiple comparisons.

Ventilatory parameters: The use of volume-regulated ventilation assured that gross tidal volume during perfluorocarbon associated gas exchange and during continuous positive pressure breathing would be comparable. Peak pressure generated by breaths of fixed volume was comparable during continuous positive pressure breathing and during perfluorocarbon associated gas exchange (Table 2). Static end-inspiratory pressure was also comparable before and during perfluorocarbon associated gas exchange. During perfluorocarbon associated gas exchange, both calculated end-inspiratory airways resistance and thoracic compliance were comparable to values determined during continuous positive pressure breathing.

TABLE 2

| | Lung mechanics during CPPB and PAGE | | | | |
|---|---|---|---|---|---|
| | CPPB | Duration of PAGE (min) | | | |
| | | 5 | 15 | 30 | 60 |
| Pmax | 22.8 ± 4.2 | 22.5 ± 2.9 | 21.8 ± 2.9 | 22.7 ± 3.2 | 21.8 ± 2.2 |
| Pei | 19.6 ± 3.4 | 18.8 ± 2.0 | 18.2 ± 1.9* | 18.7 ± 2.2 | 17.6 ± 1.6** |
| Paw | 7.3 ± 1.0 | 7.9 ± 1.1 | 7.6 ± 1.0 | 7.7 ± 0.9 | 7.4 ± 0.8 |
| ETV | 43.6 ± 8.7 | 43.7 ± 8.8 | 44.0 ± 8.7 | 43.6 ± 8.7 | 44.0 ± 8.9 |
| Ct | 3.0 ± 1.1 | 3.1 ± 0.8 | 3.2 ± 0.7 | 3.1 ± 0.8 | 3.3 ± 0.8 |
| Raw | 57 ± 21 | 66 ± 14 | 63 ± 13 | 72 ± 27 | 74 ± 26 |

Lung mechanics were virtually identical during PAGE and CPPB. Pmax = peak airway pressure, Pei = static end-inspiratory pressure, Paw = mean airway pressure, all in cm H2O. ETV = effective tidal volume delivered to the animal (ml). Ct = total thoracic compliance, calculated an ETV/(Pei-PEEP), is expressed in ml/cm H2O. Raw = end-inspiratory airway resistance, calculated as (Pmax-Pei)/flow, is expressed in cm H2O/l/sec. All values are means ± sd. *$p < .05$ and **$p < .01$ vs values during CPPB by ANOVA with Newman Keuls correction for multiple comparisons.

Figure 5:
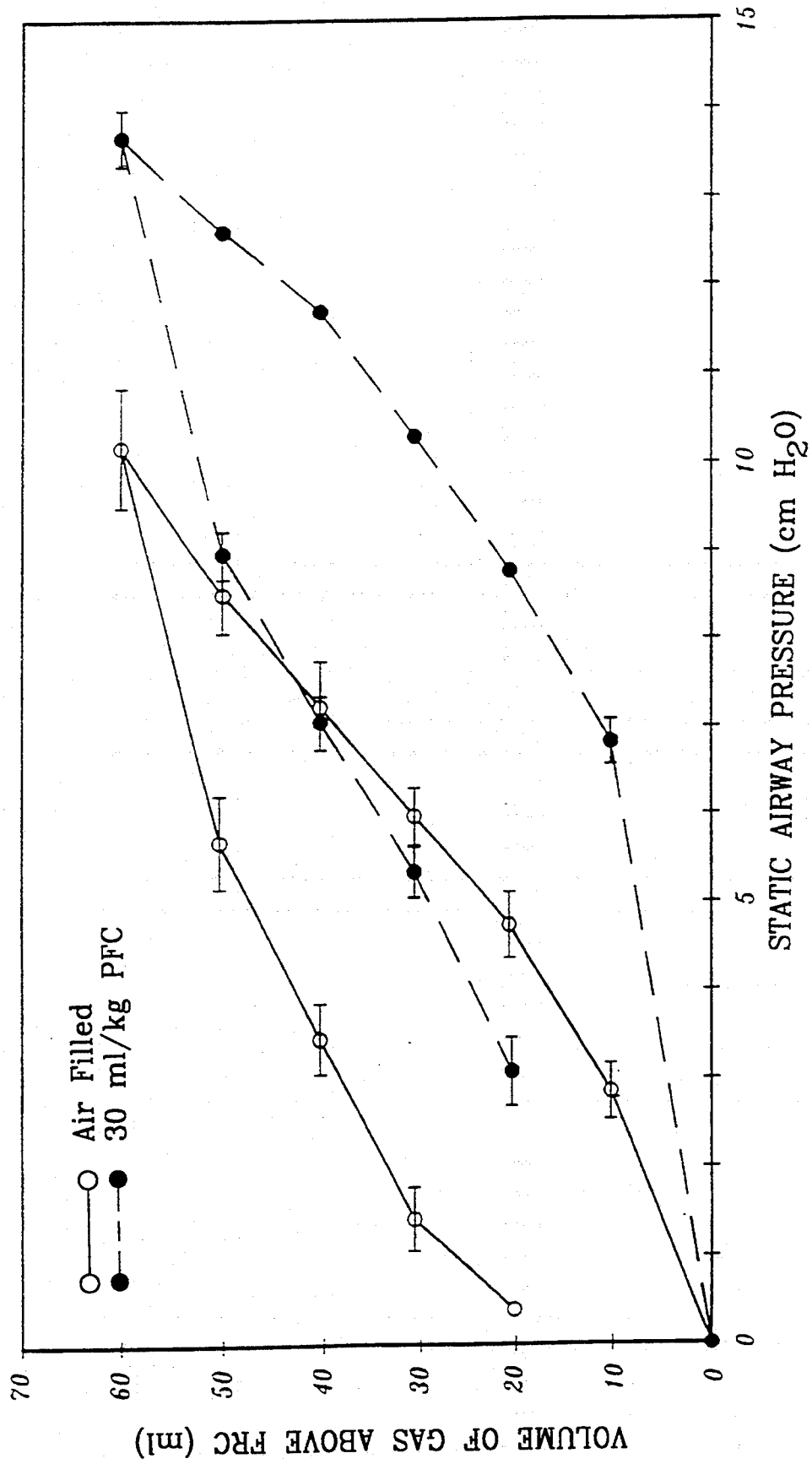
FIG. 5 presents pressure/volume curves of air-filled (open circles) and perfluorocarbon-filled (solid circles) lungs.

Pressure/volume relationship: Within the range of tidal breathing, the pressure/volume relationship was consistently altered by the presence of FC77 within the lung. Despite a total thoracic anteroposterior diameter that averaged 9.3±0.8 cm, the perfluorocarbon-filled lung generated only about 4 cm H2O more pressure for any volume of gas added above functional residual capacity than did the air filled lung (FIG. 5).

Referring to FIG. 2 in more detail, the static airway pressure required to inflate the lungs with gas to volumes above functional residual capacity (FRC), within the range of tidal breathing, was greater for the perfluorocarbon (PFC) laden lung. Air-filled and PFC-filled lungs probably have different volumes at FRC, so the origins of the two curves represent 0 volume above FRC, but do not represent identical lung volumes. The pressure/volume relationship of the perfluorocarbon-laden normal lung displays hysteresis, as does that of the air-filled lung. The pressure/volume curves of air-filled to 5 cm H2O positive end-expiratory pressure is minimally delayed by the presence of perfluorocarbon during perfluorocarbon associated gas exchange. The pulmonary time constant (Tc) is prolonged from 0.19 to 0.23 seconds during perfluorocarbon associated gas exchange. ETV=effective tidal volume delivered to the animal. Data is mean±sem. Differences are not statistically significant.

Direct observations of lung inflation: Direct inspection of lungs during perfluorocarbon associated gas exchange in open-chest postmortem animals revealed a tendency toward sequential inflation of alveoli with air. Superior lung segments inflated with gas before dependent portions. Exhalation appeared to be more even. The lungs appeared virtually airless throughout much of expiration (FIG. 1), and the cut surface of end-expiratory lung, although wet with perfluorocarbon, was bubble-free. Compression of cut sections of expiratory lung extruded fluid, but no air.

Hemodynamic variables: Perfluorocarbon associated gas exchange did not cause significant changes in heart rate, systemic arterial pressure, or right atrial pressure (Table 3). Oxygen delivery to tissues was sufficient to prevent metabolic acidosis during perfluorocarbon associated gas exchange, although venous oxygen saturation was slightly lower than that during continuous positive pressure breathing.

Were this not so, much of the pulmonary blood flow would represent an intrapulmonary shunt.

It might, however, be presumed that residual air is trapped in the lung of the closed-chest piglet at end-expiration, and that this gaseous residual volume supports expiratory gas exchange and is solely responsible for the excellent oxygenation observed in this study. FIG. 8 illustrates two possible relations of large, single bubbles to alveolar surfaces during perfluorocarbon associated gas exchange. Bubble growth within the

TABLE 3

Hemodynamic function during CPPB and PAGE

| | CPPB | Duration of PAGE (min) | | | |
|---|---|---|---|---|---|
| | | 5 | 15 | 30 | 60 |
| HR | 180 ± 37 | 182 ± 30 | 189 ± 32 | 189 ± 35 | 189 ± 38 |
| Pao | 96 ± 11 | 94 ± 11 | 94 ± 11 | 95 ± 10 | 96 ± 8 |
| Pra | 6 ± 1 | 5 ± 1 | 5 ± 1 | 6 ± 2 | 5 ± 1 |
| Sat V (%) | 79 ± 9 | 73 ± 8** | 71 ± 8** | 73 ± 6** | 73 ± 8** |

Hemodynamic measurements suggest a modest decline in cardiac output. Pao = aortic mean pressure, Pra = right atrial mean pressure, both in mm Hg. Sat V = right atrial oxygen saturation. All values are means ± sd. **p < .01 vs values during CPPB by ANOVA with Newman Keuls correction for multiple comparisons.

Discussion

This disclosure details the efficacy of perfluorocarbon associated gas exchange in normal piglets, and indicates that, in normal animals, ventilation and oxygenation can be supported almost as effectively by perfluorocarbon associated gas exchange as by continuous positive pressure breathing. Below are discussed the principles by which perfluorocarbon associated gas exchange supports oxygenation and ventilation in normal animals, the implications of elevated pulmonary surface tension, and representative applications of perfluorocarbon associated gas exchange to lungs with surfactant deficiency or dysfunction.

Gas exchange during perfluorocarbon associated gas exchange: The tidal volume of gas delivered to piglets in the present study greatly exceeded the estimated (2 ml/kg) dead space of airways. It follows that most of each 15-ml/kg breath was dispersed among terminal airways and alveoli. It appears that dispersion of inspired gas among higher generation airways and alveoli allowed intimate contact between gas and perfluorocarbon, and provided a suitable environment for in vivo "bubble-oxygenation." Otherwise, it is nearly impossible to explain the persistence of excellent oxygenation over the course of these studies, for no more than 15 ml/kg dissolved oxygen could have been instilled with the perfluorocarbon at the onset of perfluorocarbon associated gas exchange.

It was apparent on direct inspection of open-chest animals that inflation of alveoli with air during perfluorocarbon associated gas exchange was asynchronous, perhaps reflecting the airway pressure dependence of perfluorocarbon displacement by gas at differing vertical heights in the lung. Moreover, the entire lung appeared airless throughout much of expiration. Pneumotachometer measurements revealed that exhalation was 86% complete by 0.32 seconds after the onset of expiration. Thus, the lungs were virtually airless throughout the last 1.5 to 2 seconds of the 3-second respiratory cycle. In this airless state, perfluorocarbon was the sole apparent alveolar oxygen reservoir. The observation that oxygenation was excellent during perfluorocarbon associated gas exchange, despite this prolonged airless state, strongly suggests direct participation of perfluorocarbon in pulmonary gas exchange.

fluid (12A) would present two interfacial surfaces: gas/perfluorocarbon (X) and alveolar lining/perfluorocarbon (Y). Bubble growth against the alveolar lining (12B) would present an additional interface: alveolar lining/gas (Z). Inspiration (Insp) might be expected to distend surfaces in such a way as to minimize the total rise in surface forces that occurs along all of these possible interfaces. Erythrocytes (RBC) are shown in capillaries within the alveolar septum. Their capacity to take up oxygen from perfluorocarbon would be an important determinant of $PaO_2$ during perfluorocarbon associated gas exchange.

At peak inspiration, alveoli accommodate 30 ml/kg perfluorocarbon, in addition to tidal and residual gas. Blood flow through capillaries that perfuse regions of the alveolar surface adjacent to perfluorocarbon would represent an intrapulmonary right-to-left shunt, even in inspiration, if the perfluorocarbon were unable to support gas exchange. Values for $PaO_2$ during perfluorocarbon associated gas exchange are incompatible with more than 15% intrapulmonary shunt. Furthermore, the decline in $PO_2$ on instillation of perfluorocarbon and start of perfluorocarbon associated gas exchange (after correction for perfluorocarbon vapor pressure) could not represent more than a 3% to 4% increment in the intrapulmonary shunt. This increment represents the maximum intrapulmonary shunt that could be attributed to the presence within alveoli of fluid that did not participate in gas exchange.

$PaO_2$ was lower during perfluorocarbon associated gas exchange than during continuous positive pressure breathing at $FIO_2$ of 1.0. Ideal gas exchange would allow arterial $PaO_2$ to approach a theoretical alveolar value ($PAO_2$) of: $PAO_2 = FIO_2 \times (pB - pH_2O - pPFC) - pCO_2/RQ$ (wherein p is pressure, B is barometric, PFC is perfluorocarbon, and I{Q is respiratory quotient). Measured barometric pressure averaged 748±5 torr (100±0.7 kPa). If we assume an RQ of 1, theoretical $PaO_2$ would be 586 torr (78.1 kPa). Thus, the mean alveolar-arterial oxygen difference during perfluorocarbon associated gas exchange (185±50 torr (24.7±6.7 kPa)) did not differ substantially from that measured during continuous positive pressure breathing (159±61 torr (21.2±8.2 kPa)). Moreover, $PaCO_2$ during perfluorocarbon associated gas exchange was comparable to PaCO$_2$ during continuous positive pressure breathing (40±4 vs. 38±6 torr (or 5.3±0.5 vs. 5.1±0.8 kPa)). Thus, the combination of bubble-oxygenation, gas diffusion from perfluorocarbon to alveolar vessels, and ventilation/perfusion matching during perfluorocarbon associated gas exchange was not appreciably less efficient than was gas exchange during continuous positive pressure breathing.

Mechanical properties of the perfluorocarbon-laden lung: Perfluorocarbon associated gas exchange was instituted using a conventional volume-regulated, time-cycled ventilator. Minute ventilation, respiratory rate, inspiratory time, and positive end-expiratory pressure were not altered to accomplish perfluorocarbon associated gas exchange. Clinical measures of mechanical lung function were not substantially different during perfluorocarbon associated gas exchange than during continuous positive pressure breathing. Peak airway pressure was not elevated after the instillation of FC77. Nor was static end-inspiratory pressure elevated during perfluorocarbon associated gas exchange. The presence of perfluorocarbon did not have important adverse effects on mechanical function of the lung. Early in expiration, peak flow was lower during perfluorocarbon associated gas exchange than during continuous positive pressure breathing. End-inspiratory airways resistances were 68 and 57 cm H$_2$O/1/sec during perfluorocarbon associated gas exchange and during continuous positive pressure breathing, respectively. Although airways resistance was clearly higher during perfluorocarbon associated gas exchange, it did not approach values reported for 1.66 kg infant lambs during liquid ventilation (3600 cm H$_2$O/1/sec) (26). This suggests that there is little bulk movement of perfluorocarbon along airways during perfluorocarbon associated gas exchange. Most of the bulk flow that takes place during perfluorocarbon associated gas exchange must represent tidal movement of gas, and resistance to gas flow is little different during perfluorocarbon associated gas exchange than during continuous positive pressure breathing.

The pressure/volume curves of air-filled and perfluorocarbon-laden lung differed at every increment of gaseous inflation by only 4 cm H$_2$O. This was unexpected, for the average lung height (allowing 3 cm for chest and back thickness) was approximately 6 cm, and the density of the perfluorocarbon alone would create a pressure of 10.5 cm H$_2$O at end-expiration in the most dependent segments of the lung. In fact, an airway pressure of 3 to 4 cm H$_2$O was required to merely displace perfluorocarbon from the vertical portion of the endotracheal tube outside the airway. Therefore, the pressure required to displace perfluorocarbon from lung segments during bubble formation may be less than that suggested by the height of the end-expiratory fluid column within the lungs. This surprising finding probably reflects two factors: irregular shape of the lung, and interruption of the airway fluid column by gas during lung inflation.

In the gas-free perfluorocarbon-filled lung, pressure (P) generated in a dependent alveolus by the fluid above it is: P=FC77 density×fluid column height. It is reasonable to suppose that, as the lung inflates with gas, liquid continuity between vertically related lung segments is lost, for the perfluorocarbon within airways is displaced by air. To estimate the alveolar pressure that must exist within a segment to support the lung above it, one would approximate the weight of lung and perfluorocarbon above the segment and divide that weight by the cross-sectional area of the lung at that vertical height. The lung is irregular in shape, and has greater cross-sectional area dorsally (below) than ventrally (above). Therefore, its volume is less than the product of vertical height and cross-sectional area of the base. It follows that, once airways have filled with gas and fluid continuity has been lost, the contribution of perfluorocarbon weight to alveolar pressure will be less than might be suggested by vertical height of the lung.

Moreover, there are at least two other possible explanations for the rightward shift of the pressure/volume relation of the perfluorocarbon-filled lungs during inflation with gas. First, perfluorocarbon was added to the lungs as the meniscus in the tracheostomy tube fell during the hour of perfluorocarbon associated gas exchange. Some of this decrease in tracheostomy fluid level may have reflected a gradual increase in functional residual capacity during perfluorocarbon associated gas exchange. It is possible that the weight of the perfluorocarbon and its effects on end-expiratory pulmonary recoil pressure caused functional residual capacity to climb over the course of the study, and that pressure/volume curves before and after perfluorocarbon associated gas exchange were performed at somewhat different functional residual capacity. Second, it is also possible that, in addition to the 30 ml/kg perfluorocarbon instilled into the lungs at the onset of perfluorocarbon associated gas exchange, and on top of any volume of perfluorocarbon added to functional residual capacity during perfluorocarbon associated gas exchange to maintain a visible meniscus in the tracheostomy tube, some residual gas remained in the lungs of closed-chest piglets at end-expiration at ambient pressure. This could, again, have caused an elevation of the functional residual capacity from which pressure/volume curves were determined after perfluorocarbon associated gas exchange.

If either of these phenomena actually contributed to the rightward shift of the pressure/volume curve after perfluorocarbon associated gas exchange, that would further reduce the apparent significance of buoyancy of gas in perfluorocarbon to the pressure/volume relationship.

During continuous positive pressure breathing, thoracic compliance may be defined as the effective tidal volume of inflation divided by the pressure excursion with each breath from positive end-expiratory pressure to static end-inspiratory pressure. By this definition, thoracic compliance increased from 3.0 to 3.1 ml/cm H$_2$O on institution of perfluorocarbon associated gas exchange, and to 3.3 ml/cm H$_2$O over the ensuing hour. But, during perfluorocarbon associated gas exchange, the pressure/volume relationship involves forces that have no counterparts during continuous positive pressure breathing. The static pressure/volume relationship during perfluorocarbon associated gas exchange cannot be adequately described by a single quantitative compliance calculation. Nor does calculated compliance reflect "stiffness" alone during perfluorocarbon associated gas exchange. As the lung inflates, gas displaces fluid in airways, and bubbles of gas are "blown" in perfluorocarbon-filled alveoli. These bubbles displace fluid, so some of the airway pressure measured during perfluorocarbon associated gas exchange offsets the buoyancy of gas in liquid perfluorocarbon. Airway pressure also opposes the surface tension of the bubbles, their critical opening pressures, the surface tension of the alveolar lining at its perfluorocarbon or gas interface, the elasticity of the alveolar septae, and elastic properties of the thorax. The relative contributions of these forces cannot be deduced from this study, but the following comments are warranted.

First, in normal piglets, gas breathing during perfluorocarbon associated gas exchange is characterized by pressure/volume hysteresis, just as it is during air breathing and during liquid ventilation (27). Yet it is not clear that hysteresis is required for adequate gas exchange to occur during perfluorocarbon associated gas exchange. During perfluorocarbon associated gas exchange, alveoli need not be distended with gas in expiration for adequate gas exchange to occur. There is a reservoir of dissolved oxygen in the perfluorocarbon.

Second, Avery et al. (28) have shown that gaseous opening pressure can be lowered by prior instillation of saline into alveoli. When lungs were partially distended by saline, the gaseous opening pressure of excised dog lungs was lowered by 5 cm $H_2O$ relative to the opening pressure of gas-free, collapsed lungs. Presumably, the presence of fluid increases the alveolar radius of curvature that prevails prior to lung inflation. A similar effect apparently occurs during perfluorocarbon associated gas exchange, because alveoli are distended with perfluorocarbon at end-expiration, just as they are during liquid ventilation.

Figure 8A:
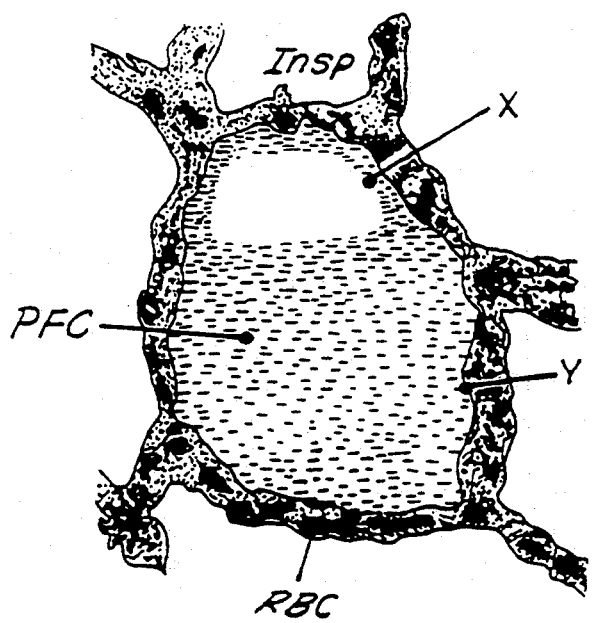
FIG. 8 depicts two possible patterns (A,B and C,D) of bubble growth within a perfluorocarbon fluid-filled alveolus.
Figure 8B:
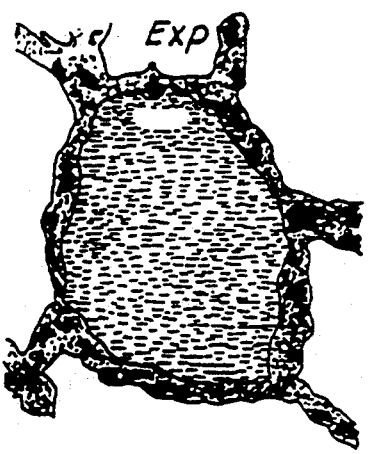
Figure 8C:
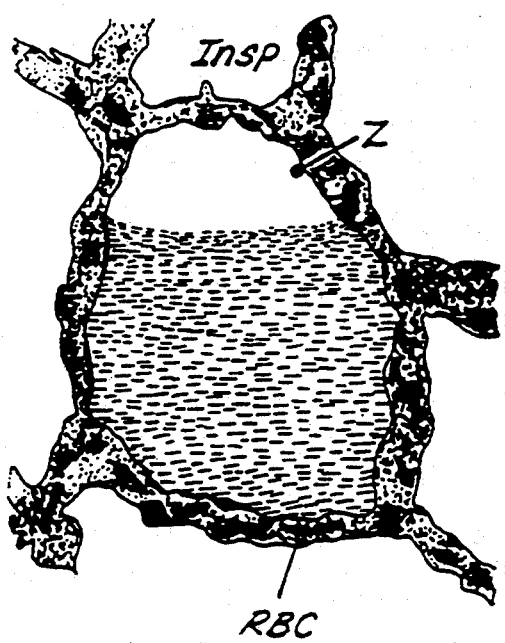
Figure 8D:
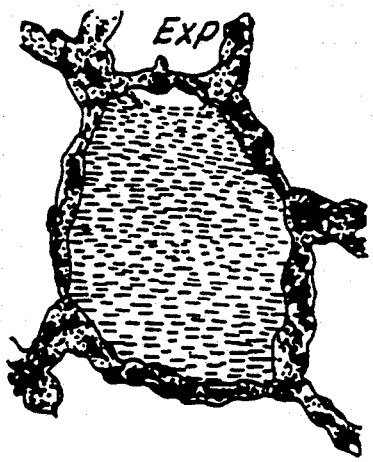

Moreover, during perfluorocarbon associated gas exchange, if the lung is (as it appears to be) virtually airless at end-expiration, the opening pressure that opposes gas inflation should be that of bubble formation. Bubble formation should be initiated in perfluorocarbon-filled distal airways and therefore involve primarily the perfluorocarbon/gas interface. Surface tension along the alveolar lining should, in the perfluorocarbon-filled alveolus, contribute little to the opening forces associated with bubble formation. It appears that the modest airway pressures measured in this study may suffice to offset the opening forces intrinsic to that interface, regardless of alveolar surface tension. Third, in normal lungs, alveolar surface tension is so low that bubbles might be expected to grow during inspiration (after initial formation) against the surface tension of the alveolar lining, rather than within the perfluorocarbon (FIG. 8C,D). This may not be the case in surfactant deficiency or dysfunction. Bubble growth could, in the surfactant deficient lung, occur by a different mechanism, within the perfluorocarbon (FIG. 8A,B). Therefore, the compliance of a normal lung may exceed that of a surfactant-deficient lung during perfluorocarbon associated gas exchange, and it cannot be assumed that adequate ventilation will occur in surfactant deficient lungs at airway pressures as low as those measured in this study.

During perfluorocarbon associated gas exchange, inspiratory alveolar distension must be opposed by surface forces acting along the alveolar lining, the same as during continuous positive pressure breathing and during spontaneous breathing. At the alveolar lining/perfluorocarbon interface, these forces should be minor, even in surfactant deficiency. This is a possible explanation for the improvement in lung compliance deserved during liquid ventilation in surfactant-deficient animals.

However, if surfactant-deficient lungs were subjected to perfluorocarbon associated gas exchange, and if bubbles were not separated from the alveolar lining by perfluorocarbon as the lung inflated, greater forces could develop along alveolar lining/gas interfaces (see "Z" in FIG. 8C). It is reasonable to speculate that bubbles will expand within perfluorocarbon-filled alveoli in such a way that they are least opposed by surface forces. If surface forces at an alveolar lining/gas interface did exceed those at the gas/perfluorocarbon interface ("X" in FIG. 12), one might expect bubbles to expand within the lower surface tension perfluorocarbon. The surface tension of the gas/perfluorocarbon interface (14 dynes/cm) is substantially lower than would be experienced at an air/water interface in the complete absence of any surfactant effect (70 dynes/cm). It is also well below the range of surface tensions measured in lungs of infants who died of the Respiratory Distress Syndrome of prematurity. Fluid derived from lungs of such infants generally have surface tensions between 20 and 30 dynes/cm at minimal film area and between 50 and 60 dynes/cm at maximal film area (29).

One further influence on the pressure/volume relationship warrants discussion. During perfluorocarbon associated gas exchange, bubble growth might take place adjacent to the alveolar lining, regardless of alveolar surface tension, because of its large radius of curvature. If this were true, bubble growth at the alveolar lining would distend the large, low surface tension alveolar lining/perfluorocarbon interface ("Y" in FIG. 8A), as well as the alveolar lining/gas interface, even in surfactant-deficient lungs. Were this the case, adequate gas exchange might occur at distending pressures as low as those measured in this study, even in surfactant deficiency.

Fortuitous properties of perfluorocarbon associated gas exchange: A host of as yet ill-defined properties contribute to the efficacy of perfluorocarbon associated gas exchange in the normal piglet. Adequacy of gas exchange during perfluorocarbon associated gas exchange is fundamentally dependent on "even" bubble-oxygenation of perfluorocarbon, and matching of any "unevenness" in this process to concomitant "unevenness" of pulmonary perfusion. For instance, if bubble formation was greatly favored in superior lung segments, perfusion would have to be comparably maldistributed, or blood flow to the dependent lung would act as an intrapulmonary right-to-left shunt and create severe arterial hypoxemia. A severe nonuniformity of bubbling, even were it perfectly mirrored by redistribution of perfusion, would greatly restrict the cross-sectional area of lung vasculature able to participate in pulmonary blood flow and, thus, adversely affect pulmonary circulation. The limited hemodynamic data presented above does not suggest that perfluorocarbon associated gas exchange severely impedes pulmonary blood flow. Therefore, the efficiency of ventilation/perfusion matching and gas exchange during perfluorocarbon associated gas exchange is rather surprising.

Liquid ventilation, perfluorocarbon associated gas exchange, and disorders of surface tension: Resumption of air breathing is readily accomplished after liquid ventilation. Typically, at the termination of liquid ventilation, animals have been drained of perfluorocarbon to restore gaseous functional residual capacity before resumption of continuous positive pressure breathing. However, the process of draining perfluorocarbon after liquid ventilation is incomplete. Calderwood et al. (30) noted that 200 to 400 ml of perfluorocarbon was retained in the lungs of 10- to 19-kg dogs, despite attempted complete drainage. Shaffer et al. (31) reported retention of 5 ml/kg in premature lambs after instillation of volumes equivalent to measured functional residual capacity. While this situation differs from circumstances during perfluorocarbon associated gas exchange, in which 30 ml/kg perfluorocarbon is instilled into the trachea and left in situ, data from experience in the resumption of continuous positive pressure breathing after liquid ventilation (see below) indicates there may be special clinical applications for perfluorocarbon associated gas exchange in surfactant deficiency or dysfunction.

Function of normal lungs does not appear to be enhanced by perfluorocarbon exposure during liquid ventilation, yet pulmonary function after drainage is virtually normal (32), despite complete radiographic opacity of the lung fields (33). In premature animals, however, retention of perfluorocarbon does improve lung function. Studies of minipigs (95 day gestation) showed a 2- to 3-fold increase in lung compliance on return to air breathing after 20 minutes of liquid ventilation; these measurements approach those of the mature lung (9). Shaffer et al. (34) studied liquid ventilation in lambs of 135 to 138 days gestation with clinical RDS, and observed that peak intratracheal pressures were lower when continuous positive pressure breathing was resumed after liquid ventilation than before ($25\pm8$ vs. $36\pm6$ cm $H_2O$). In lambs of similar gestation, Shaffer et al. (12) found that lung compliance and peak tracheal pressure were significantly improved on reinstitution of continuous positive pressure breathing after liquid ventilation, and that airway resistance was unchanged. $PaO_2$ was greater and $PaCO_2$ was lower when continuous positive pressure breathing was reinstituted after liquid ventilation than either before or during liquid ventilation. In premature lambs of similar gestation whose births were complicated by meconium aspiration (35), arterial $PaO_2$ and $PaCO_2$ improved on resumption of continuous positive pressure breathing after liquid ventilation, when compared to values either before or during liquid ventilation.

These favorable effects of perfluorocarbon retention on gas exchange and mechanical lung function in immature animals indicate that perfluorocarbon associated gas exchange may prove effective in surfactant deficiency and dysfunction.

Impediments to clinical applications of liquid ventilation: One of the important impediments to clinical introduction of liquid ventilation techniques has been the complexity and experimental nature of the instrumentation required for extracorporeal gas processing and cycling of perfluorocarbon into and out of the lungs. In these respects, perfluorocarbon associated gas exchange is less complex and less dramatic an innovation than liquid ventilation, because the subject method uses a conventional ventilator to process perfluorocarbon within the lung.

Citations (1) Klystra, J. A., et al., Of mice and fish, *Transactions of the American Society for Artificial Internal Organs* 8:378–383, 1962.

(2) Reufer, R., Surfactant and alveolar surface forces after breathing of an inert fluoridated liquid, *Federation Proceedings* 29(5):1813–1815, 1970.

(3) Clark, L. C., and F. Gollan, Survival of mammals breathing organic liquids equilibrated with oxygen at atmospheric pressure, *Science* 152:1755–1756, 1966.

(4) Biro, P. B., and P. Blais, Perfluorocarbon blood substitutes, *CRC Critical Reviews in Oncology/Hematology* 6(4):311–374, 1987.

(5) Modell, J. H., et al., Long-term survival of dogs after breathing oxygenated perfluorocarbon liquid, *Federation Proceedings* 29(5): 1731–1739, 1970.

(6) Modell, J. H., et al., Liquid ventilation of primates, *Chest* 69:79–81, 1976.

(7) Calderwood, H. W., et al., Residual levels and biochemical changes after ventilation with perfluorinated liquid, *Journal of Applied Physiology* 139:603–607, 1975.

(8) Forman, D., et al., A fine structure study of the liquid-ventilated new rabbit, *Federation Proceedings* 43:647, 1984.

(9) Ruler, R., and L. Sbitzer, Liquid ventilation in the respiratory distress syndrome, *Chest* 66(Suppl):29–30, 1974.

(10) Puchetti, B., et al., Liquid ventilation in man: first clinical experiences on pulmonary unilateral washing fluorocarbon liquid, Fourth World Congress for Bronchology (Abstracts), p. 115, 1984.

(11) Shaffer, T. H., A brief review: liquid ventilation, *Undersea Biomedical Research* 14(2):169–179, 1987.

(12) Shaffer, T. H., et al., The effects of liquid ventilation on cardiopulmonary function in preterm lambs, *Pediatric Research* 17:303–306, 1983.

(13) Shaffer, T. H., et al., Physiological effects of ventilation with liquid fluorocarbon at controlled temperatures, *Undersea Biomedical Research* 11(3):287–298, 1984.

(14) Lowe, C. A., and T. H. Shaffer, Increased pulmonary vascular resistance during liquid ventilation, *Undersea Biomedical Research* 8(4):229–238, 1981.

(15) Gollan, F., and L. C. Clark, Prevention of bends by breathing an organic liquid, *Transactions of the Association American Physicians* 29:102–109, 1967.

(16) Sass, D. J., et al., Liquid breathing: prevention of pulmonary arterio-venus shunting during acceleration, *Journal of Applied Physiology* 32:451–455, 1972.

(17) Sekins, K., et al., International Publication No. WO 91/03267.

(18) Avery, M. E., and J. Mead, Surface properties in relation to atelectasis and hyaline membrane disease, *Am J Dis Child* 97:517, 1959.

(19) Pattle, R. E., et al., Inability to form a lung-lining film as a cause of the respiratory-distress syndrome in the newborn, *Lancet* ii:469, 1962.

(20) Holm, B. A., and S. Matalon, Role of pulmonary surfactant in the development and treatment of adult respiratory distress syndrome, *Anesth Analg* 69(6):805, 1989.

(21) Curtis, S. E., et al., Airway and alveolar pressures during perfluorocarbon breathing in infant lambs, *J Appl Physiol* 68(6):2322, 1990.

(22) Curtis, S. E., et al., Cardiac output during liquid (perfluorocarbon) breathing in newborn piglets, *Crit Care Meal* 19(2):225–230, 1991.

(23) Wolfson, M. R., et al., A new experimental approach for the study of cardiopulmonary physiology during early development, *J Appl Physiol* 65(3):1436, 1988.

(24) Greenspan, J. S., et al., Liquid ventilation of human preterm neonates, *J Pediatr* 117(1 part 1):106, 1990.

(25) Fuhrman, B. P., Perfluorocarbon liquid ventilation: the first human trial, *J Pediatr* 117(1 Part 1):73, 1990.

(26) Shaffer, T. H., et al., Cardiopulmonary function in very preterm lambs during liquid ventilation, *Pediatr Res* 17:680, 1983.

(27) Barrow, R. E., Volume-pressure cycles from air and liquid filled intact rabbit lungs, *Respiration Physiology* 63:19, 1986.

(28) Avery, M. E., et al., The inflationary force produced by pulmonary vascular distension of excised lungs: the possible relation of this force to that needed to inflate the lungs at birth, *J Clin Invest* 38:456, 1959.

(29) Avery, M. E., and B. D. Fletcher, The Lung and Its Disorders in the Newborn Infant, Third Edition, Philadelphia, W B Saunders, p. 216, 1974.

(30) Calderwood, H. W., et al., Pulmonary lavage with liquid fluorocarbon in a model of pulmonary edema, *Anesthesiology* 38(2):141A, 1973.

(31) Shaffer, T. H., et al, Pulmonary lavage in preterm lambs, *Pediatr Res* 12:695, 1978.

(32) Shaffer, T. H., and G. D. Moskowitz, Demand-controlled liquid ventilation of the lungs, *J Appl Physiol* 36:208, 1974.

(33) Gollan, F., et al, Compliance and diffusion during respiration with fluorocarbon fluid, *Federation Proceedings* 29(5):1725, 1970.

(34) Shaffer, T. H., et al., Gaseous exchange and acid-base balance in premature lambs during liquid ventilation since birth, *Pediat Res* 10:227, 1976.

(35) Shaffer, T. H., et al., Liquid ventilation: effects on pulmonary function in distressed meconium-stained lambs, *Pediat Res* 18(1):47, 1984.

While the present invention has been described in conjunction with a preferred embodiment and illustrative examples, one of ordinary skill after reading the foregoing specification will be able to effect various changes, substitutions of equivalents, and other alterations to the subject matter set forth herein. It is therefore intended that the protection granted by Letters Patent hereon be limited only by the definition contained in the appended claims and equivalents thereof.

The embodiments of the invention in which an exclusive property or privilege is claimed are defined as follows:

1. A method for maintaining respiratory gas exchange, comprising the steps of:
    first introducing into the pulmonary air passages of a mammalian host a volume of perfluorocarbon liquid from about 50% to not more than about 100% of the pulmonary functional residual capacity of the host; and
    then physically admixing a volume of breathing gas with said introduced volume of perfluorocarbon liquid in the pulmonary air passages whereby said breathing gas forms bubbles inside said liquid-containing pulmonary air passages so that oxygenation of said perfluorocarbon liquid takes place in vivo, said admixing resulting when said host takes multiple breaths of a breathing gas.

2. The method of claim 1, wherein continuous positive pressure gas breathing is provided into a patient's perfluorocarbon liquid-containing pulmonary air passages by a volume-regulated, timed-cycle gas respirator or a pressure-limited, timed-cycle gas respirator.

3. The method of claim 1, wherein the volume of perfluorocarbon liquid is maintained substantially equivalent to the pulmonary functional residual capacity of a host throughout the treatment period.

4. The method of claim 1, wherein after the treatment period the perfluorocarbon liquid is removed from a patient's air passages by evaporation.

5. The method of claim 1, wherein the perfluorocarbon liquid comprises a pharmacologic or diagnostic agent.

6. The method of claim 1 wherein the volume of perfluorocarbon liquid introduced into a patient's pulmonary air passages is at least about $\frac{1}{2}$ of the pulmonary functional residual capacity of the host.

7. The method of claim 1 wherein the volume of perfluorocarbon liquid introduced into a patient's pulmonary air passages is at least about $\frac{3}{4}$ of the pulmonary functional residual capacity of the host.

8. The method of claim 1, wherein said breathing gas is moved into and out of the host's lungs by a gas ventilator.

9. The method of claim 1, wherein said perfluorocarbon liquid is halogenated.

10. The method of claim 1, wherein said perfluorocarbon liquid is perfluorooctyl bromide.

11. The method of claim 1, wherein said introducing step is performed on a host having pulmonary surfactant deficiency or dysfunction.

12. The method of claim 1, wherein said introducing step is performed on a host in need of resuscitation.

13. The method of claim 12, wherein said resuscitation is cardiopulmonary resuscitation.

14. A device for regulating fluid flow during perfluorocarbon associated gas exchange, comprising:
    first and second conduits having distal and proximal ends,
    an endotracheal tube,
    a chamber adapted for establishing fluid communication between said endotracheal tube and said conduits, said chamber interposed between said conduits and said endotracheal tube, at least one valve connected to said conduits to reversibly establish fluid communication between said chamber and either the proximal end of the first but not the second conduit, or the proximal end of the second but not the first conduit,
    means associated with said first conduit to introduce and remove a perfluorocarbon liquid to and from said chamber and into a lung,
    and means associated with said second conduit to introduce and remove breathing gas separate and apart from said perfluorocarbon liquid to and from said chamber to permit a patient into whom the endotracheal tube is introduced to breathe a breathing gas into and out of perfluorocarbon-containing pulmonary passages into which said perfluorocarbon liquid has been introduced by said device.

15. The device of claim 14, wherein the first conduit comprises first, second, and third channels having proximal ends that collectively establish fluid communication with the chamber as regulated by the valve means.

16. The device of claim 14, wherein the second conduit comprises a single channel having an aperture to the ambient environment.

17. The device of claim 16, wherein the valve means opens the aperture to the ambient environment when fluid communication is established between the chamber and the first but not the second conduit, and closes the aperture when fluid communication is established between the chamber and the second but not the first conduit.

18. A system for implementing perfluorocarbon associated gas exchange, comprising:
a device for first introducing perfluorocarbon liquid into a patient's pulmonary air passages,
a gas ventilator for maintaining respiratory gas exchange in a patient's perfluorocarbon liquid-containing pulmonary air passages including means for secondly introducing and removing multiple breaths of breathing gas into said passages during a treatment period separate and apart from said introduction of said perfluorocarbon liquid so that said breathing gas physically admixes with said perfluorocarbon liquid in said pulmonary air passages, of a patient whereby a patient's pulmonary air passages simultaneously contain both said breathing gas and said perfluorocarbon liquid, and
a device operably associated with both said introducing device and said gas ventilator for regulating the aforesaid introduction of liquid and introduction and removal of gas during the treatment period.

* * * * *

UNITED STATES PATENT AND TRADEMARK OFFICE
CERTIFICATE OF CORRECTION

PATENT NO. : 5,437,272
DATED : August 1, 1995
INVENTOR(S) : Bradley P. Fuhrman

It is certified that error appears in the above-identified patent and that said Letters Patent is hereby corrected as shown below:

Title page, item [73], Assignee: should read-- University of Pittsburgh of the Commonwealth System of Higher Education, 911 William Pitt Union, Pittsburgh, PA Signed and Sealed this Sixteenth Day of January, 1996

*Attest:*

BRUCE LEHMAN

*Attesting Officer*     *Commissioner of Patents and Trademarks*